United States Patent [19]
Humphreys et al.

[11] Patent Number: 5,919,639
[45] Date of Patent: Jul. 6, 1999

[54] Ii PEPTIDE THERAPEUTICS TO ENHANCE ANTIGEN PRESENTATION

[75] Inventors: Robert E. Humphreys, Acton; Sharlene Adams, Worcester; Minzhen Xu, Northborough, all of Mass.

[73] Assignee: University of Massachusetts, Boston, Mass.

[21] Appl. No.: 08/968,676

[22] Filed: Nov. 12, 1997

Related U.S. Application Data

[62] Division of application No. 08/670,605, Jun. 26, 1996, abandoned.

[51] Int. Cl.$^6$ .............................. C12N 5/06; C07K 7/00; A61K 38/10
[52] U.S. Cl. ..................... 435/7.24; 424/185.1; 514/2; 514/13; 514/14; 514/15; 514/16; 514/17; 514/18; 435/7.1; 436/501; 436/507
[58] Field of Search ..................... 514/2, 13–18; 435/7.1, 7.24; 436/501, 507; 424/185.1

[56] References Cited

U.S. PATENT DOCUMENTS

| | | |
|---|---|---|
| 5,023,233 | 6/1991 | Nutt et al. . |
| 5,510,240 | 4/1996 | Lam et al. . |
| 5,559,028 | 9/1996 | Humphreys . |

FOREIGN PATENT DOCUMENTS

94/26773  11/1994  WIPO .

OTHER PUBLICATIONS

Gautam et al., *Proceedings of the National Academy of Sciences USA 92:* 335–339 (1995).
Chicz et al., *Nature 358:* 764–768 (1992).
Geluk et al., *Molecular Immunology 32* No. 13: 975–981 (1995).
Malcherek et al., *J. Exp. Med. 181:* 527–536 (1995).
Seete et al., *Science 258:* 1081–1804 (1992).
Weenik et al International Immunol. 9:317 1997.
Adams et al. Eur. J. Immunol. 25: 1693–1702, Jun. 1995.

*Primary Examiner*—Thomas M. Cunningham
*Assistant Examiner*—Martha Lubet
*Attorney, Agent, or Firm*—Kevin M. Farrell

[57] ABSTRACT

Disclosed is a class of compounds referred to herein as effector compounds. Effector compounds are useful in connection with the modulation of an immune response. Modulation refers to the ability of the effector compounds of the present invention to either enhance (antigen supercharging) or inhibit (immunosuppressant activities) antigen presentation, depending upon the nature of the particular effector compound and the therapeutic context. Effector compounds include peptides, modified peptides and peptidomimetics. Also disclosed are methods for modulating presentation of an MHC class II restricted antigenic peptide to a T cell. Also disclosed are effector compounds demonstrated to act specifically on a human MHC class II allele. Also disclosed is a second class of compounds, referred to herein as immunomodulatory organic compounds. Such compounds are identified by a method which includes the following steps: providing a first complex comprising an MHC class II molecule to which an antigenic peptide has been bound; contacting the first complex with mammalian Ii key peptide LRMKLPKPPKPVSKMR (SEQ ID NO:1) (or modifications thereof including peptidomimetics), thereby forming a second complex; and screening organic molecules for compounds which bind to the second complex but not to the first complex, and which exhibit immunomodulatory activity. Compounds identified in this manner can be used to modulate an immune response in a mammal.

8 Claims, No Drawings

Ii PEPTIDE THERAPEUTICS TO ENHANCE ANTIGEN PRESENTATION

This is a divisional of application Ser. No. 08/670,605 filed Jun. 26, 1996 (now abandoned).

BACKGROUND OF THE INVENTION

The immune response to specific antigens is regulated by the recognition of peptide fragments of those antigens by T lymphocytes. Within an antigen presenting cell (APC), peptide fragments of a proteolytically processed antigen become bound into the antigenic peptide binding site of major histocompatibility complex (MHC) molecules. These peptide-MHC complexes are then transported to the cell surface for recognition (of both the foreign peptide and the adjacent surface of the presenting MHC molecule) by T cell receptors on helper or cytotoxic T lymphocytes. That antigen-specific recognition event initiates the immune response cascade for either protective or deleterious immune responses.

Two classes of MHC molecules function as immune system presenters of antigenic peptides to T cells. MHC class I molecules receive peptides from endogenously synthesized proteins, such as an infectious virus, in the endoplasmic reticulum about the time of synthesis of the MHC class I molecules. The MHC class I-bound antigenic peptides are presented at the cell surface to CD8-positive cytotoxic T lymphocytes, which then become activated and can kill the virus-expressing cells directly. In contrast, MHC class II molecules are synthesized in the endoplasmic reticulum with their antigenic peptide binding sites blocked by the invariant chain protein (Ii). These MHC class II-Ii protein complexes are transported from the endoplasmic reticulum to a post-Golgi compartment where Ii is released by proteolysis and a specific antigenic peptide becomes bound to the MHC class II molecule.

The Ii protein is cleaved by intracellular proteases through a series of fragments, some of which remain associated with the MHC class II molecules. This series of Ii fragments has been better defined through the treatment of cultured, [$^{35}$S] methionine-labeled cells with certain protease inhibitors. For example, leupeptin and antipain block the action of respective classes of proteases on Ii, and on Ii fragments which remain associated with the MHC class II alpha and beta chains. The MHC class II-bound fragments of Ii are recognized after immunoprecipitations with anti-MHC class II antibodies and/or anti-Ii antibodies, gel electrophoresis and autoradiography. In vitro cleavages of immunopurified MHC class II alpha, beta-Ii protein complexes with cathepsin B, cathepsin D, and other proteases, define site specific cleavages by individual enzymes. The MHC class II alpha, beta chains are relatively resistant to proteolysis.

These specific cleavage sites in Ii have been confirmed at a molecular level with Ii mutants having amino acid replacements at putative sites for proteolysis. Several cleavage sites were defined. The crucial site for understanding the mechanism of the compounds of this invention is in a region of clustered cationic-hydrophobic dipeptidyl units in human Ii (77–92) (Lu et al, *J. Biol. Chem.* 145: 899–904, (1990)). Mutation at each of these four, redundant cleavage sites in the mutant Ii[$R^{78}{\to}A$; $K^{80}{\to}A$; $K^{83}{\to}A$; $K^{86}{\to}T$] blocks cleavage in that region (Xu et al., *Molecular Immunology* 31: 723–731 (1994)).

The region with these clustered, apparent cleavage sites lies in the primary sequence of Ii about the positions of N-termini of a series of naturally occurring Ii fragments, the CLIP peptides. The CLIP peptides occur naturally in isolated MHC class II molecules and are abundantly presented in MHC class II molecules of a mutant cell line which is deficient in some mechanism which regulates antigenic peptide charging into MHC class II molecules. This last finding has led to the hypotheses that the CLIP peptides are an intermediate in peptide charging into MHC class II molecules (Roche, P., and Cresswell, P., *Nature* 345: 615–619 (1990)), or represent a default pathway to block such molecules from accepting ambient peptides after charging with an APC-selected peptide has failed (Xu et al. in *Antigen Processing and Presentation*, Humphreys, R. E., ed.: 228–242, Academic Press, NY (1994)).

Overlap among the MHC class II molecule binding sites for antigenic peptide, the Ii-CLIP peptides, and the therapeutic Ii-key peptide, is being determined by x-ray crystallography at a molecular level. The exact position of influenza virus hemagglutinin peptide HA307-319 in the antigenic peptide binding groove HLA-DR1 was determined first (Stern et al., *Nature* 368: 215–221 (1994)). Subsequently, the exact positioning of a CLIP peptide in the same antigenic peptide binding groove was determined (Ghosh et al., *Nature* 378: 457–462 (1995)). In both cases, the peptides assumed the conformation of a polyprolyl type II helix in the antigenic peptide binding groove. The backbone atoms of the CLIP peptide overlay exactly the positions of the backbone atoms of the HA peptide, with comparable placement of side chains into pockets of the MHC class II molecule. Residue position $M^{91}$ of the CLIP peptide overlays the first residue position of the HA peptide. The CLIP residues N-terminal to $M^{91}$, extending back to $P^{87}$ were also in a polyprolyl type II helix conformation. More N-terminal residues, including positions human Ii $L^{77}$-$K^{83}$ were not resolved in those crystallographic studies, but clearly lie outside the antigenic peptide binding groove, along the side of the MHC class II molecule.

Thus, although much has been learned with respect to the interaction of molecules in the antigen presentation process, the application of relevant findings to therapeutic ends remains, for the most part, unrealized.

SUMMARY OF THE INVENTION

The present invention relates, in one aspect, to a class of compounds referred to herein as effector compounds. Effector compounds are useful in connection with the modulation of an immune response. Modulation refers to the ability of the effector compounds of the present invention to either enhance (antigen supercharging), or inhibit (immunosuppressant activities) antigen presentation, depending upon the nature of the particular effector compound, and the therapeutic context.

Effector compounds include peptides and modified peptides. In a preferred embodiment, the invention relates to the mammalian Ii key peptide LRMKLPKPPKPVSKMR (SEQ ID NO:1) and modifications thereof, the peptide YRMKLP-KPPKPVSKMR (SEQ ID NO:2) being specifically excluded. Modifications specifically demonstrated include, for example, the deletion of amino acids from the N-terminus; the deletion of amino acids from the C-terminus; the protection of the C-terminus; the protection of the N-terminus; N-terminal extensions; substitutions; and cyclized derivatives. The invention also encompasses peptidomimetic structures which are structurally and functionally related to the effector compounds listed above.

Thus, the present invention relates to methods for enhancing presentation of an MHC class II restricted antigenic peptide to a T cell. Such methods include contacting the following components under physiological conditions: an MHC class II expressing antigen presenting cell; the mammalian Ii key peptide LRMKLPKPPKPVSKMR (SEQ ID NO:1) or modifications thereof (the peptide YRMKLPKPPKPVSKMR (SEQ ID NO:2) being specifically excluded); the MHC class II restricted antigenic peptide which, when added to the incubation mixture, is not in association with an antigen presenting cell; and a T cell which is responsive to the MHC class II restricted antigenic peptide.

In another aspect, the present invention relates to methods for inhibiting presentation of an MHC class II restricted antigenic peptide to a T cell. Such methods include contacting the following components under physiological conditions and incubating for an appropriate period: an MHC class II expressing antigen presenting cell displaying on its surface a T cell-presented epitope from a native protein antigen; and mammalian Ii key peptide LRMKLPKPPKPVSKMR (SEQ ID NO:1) and modifications thereof (the peptide YRMKLPKPPKPVSKMR (SEQ ID NO:2) being specifically excluded).

In other embodiments, the invention relates to effector compounds (i.e., peptides, modified peptides or peptidomimetics) which induces release of an antigenic peptide specifically from a human MHC class II allele in the absence of another antigenic peptide which binds to the human MHC class II allele. A preferred embodiment is the peptide YRMKLPKSAKPVSQMR (SEQ ID NO:3), or deletion modifications wherein from 0 to 4 amino acid residues are deleted from the C-terminus and from 0 to 6 amino acid residues are deleted from the N-terminus.

The invention also relates to an effector compound which induces release of a first antigenic peptide from a human MHC class II allele in the presence of a second antigenic peptide which binds to the human MHC class II allele. Other specific embodiments include effector compounds which bind allosterically to modulate antigenic peptide binding into the antigenic peptide binding site of human MHC class II molecules; allele-specific modulators of antigen presentation; and locus-specific modulators of antigen presentation.

The present invention also relates to a second class of compounds, referred to herein as immunomodulatory organic compounds. Such compounds are identified by a method which includes the following steps: providing a first complex comprising an MHC class II molecule to which an antigenic peptide has been bound; contacting the first complex with mammalian Ii key peptide LRMKLPKPPKPVSKMR (SEQ ID NO:1) (or modifications thereof including peptidomimetics), thereby forming a second complex; and screening organic molecules for compounds which bind to the second complex but not to the first complex, and which exhibit immunomodulatory activity. Compounds identified in this manner can be used to modulate an immune response in a mammal.

DETAILED DESCRIPTION OF THE INVENTION

U.S. application Ser. No. 08/064,400, the disclosure of which is incorporated herein by reference, disclosed the fact that a modified mammalian Ii key peptide (YRMKLPKPPKPVSKMR) (SEQ ID NO:2) had the ability to enhance presentation of an MHC class II restricted antigenic peptide to a T cell. The present invention is based, in one aspect, on the surprising discovery that the mammalian Ii key peptide is remarkably tolerant to a broad range of amino acid substitutions, deletions and insertions. This tolerance was observed in multiple assay contexts, described below, which are intended to mimic a variety of in vivo situations. In addition to this wide range of tolerance, individual peptides within the group described below were demonstrated to have remarkable MHC class II species, locus and allele specificities. Given the present disclosure, routine experimentation will lead to the development of novel therapeutic methods which are described more fully below. Although the bulk of data reported herein were generated in experiments employing murine indicator assays for biological activity, the fundamental principles have been extended to studies with purified human MHC class II molecules (Example 7) and routine experimentation will permit rapid identification of optimal structures for application to the diagnosis and treatment of human diseases.

The wild-type human Ii key peptide is LRMKLPKPPKPVSKMR. In U.S. application Ser. No. 08/064,400, tyrosine (Y) had been substituted for the wild-type N-terminal reside, leucine (L). The subject invention relates to the mammalian Ii key peptide LRMKLPKPPKPVSKMR (SEQ ID NO:1), as well as modifications thereof, the prior art peptide YRMKLPKPPKPVSKMR (SEQ ID NO:2) being specifically excluded. The use of the language "modifications thereof" to describe peptides of the present invention, while indefinite in some contexts, is appropriate given the experimental data described herein which demonstrates the many types of modifications which can be made to the Ii key peptide without eliminating its desirable properties.

The experiments described below demonstrated, for example, that the following classes of modifications failed to eliminate certain desirable properties of the YRMKLPKSAKPVSQMR (SEQ ID NO:3) peptide (a modification of the peptide LRMKLPKPPKPVSKMR (SEQ ID NO:1)): deletion of amino acids from the N-terminus; deletion of amino acids from the C-terminus; protection of the C-terminus; protection of the N-terminus; N-terminal extensions; substitutions; and cyclized derivatives. In the paragraphs which follow, the classes of modification will be considered in greater detail, as will the assay formats on which the conclusions are based. The desirable properties mentioned above include immunosuppressant (see Example 6, Tables 29–34) and antigen supercharging activities (see Examples 1–4, Tables 1–18), depending upon the experimental context.

In addition to peptides and modifications thereof, the present invention also encompasses a class of organic compounds commonly referred to as peptidomimetic structures. Such structures, which demonstrate MHC class II contact points similar to those of the peptides and modified peptides of the invention, can be identified through routine experimentation. Such compounds may exhibit either equivalent, or superior properties (relative to disclosed peptides). Such properties include, for example, potency, bioavailability and other pharmacokinetic properties, MHC class II locus and allele specificity. Such organic compounds can be synthesized by directed design methods given the structure-function relationships revealed in this disclosure and/or through additional routine experimental efforts. Such compounds can also be identified through screening procedures on organic compounds from either existing libraries of such structures or libraries which are created, for example, by methods of combinatorial chemistry or genetics. Certain atoms or functional groups in such compounds will overlay, in three dimensional space, atoms or functional groups of active peptides of the type disclosed herein. Both configurations are structured at the active regulatory site of contact of such compounds on the MHC class II molecule, either in a resting or transition state. The class of compositions which include both peptides and modified peptides, as well as structurally-related peptidomimetics, are referred to herein as "effector compounds".

Examples 1–4 (Tables 1–18) will be briefly considered in order to establish the concept of tolerance discussed above. These examples describe experimental results observed in the so-called "simultaneous" assay. In the simultaneous assay four principle components are cultured together for a 24 hour period. The components of this culture, which are added simultaneously, are: (a) an antigenic peptide characterized by the ability to bind specifically into the antigenic peptide binding groove of an MHC class II molecule, (b) mitomycin C-treated, MHC class II-positive antigen presenting cells (APC) bearing the MHC class II allele required for binding of the specific antigenic peptide, and presentation of the specific antigenic peptide to the antigenic peptide-specific T cell hybridoma, (c) an effector compound of the present invention, and (d) an MHC class II allele-restricted T cell hybridoma specific for the antigenic peptide and the MHC class II allele restricting its presentation. Following incubation of this primary culture, an aliquot of its supernatant is transferred into a second culture well for incubation with an interleukin-dependent lymphoblastoid cell line. The degree of stimulation of that second, indicator cell by the interleukins which had been released from the activated T cell hybridoma in the primary culture is measured by quantitating tritiated thymidine deoxyribose $\{[^3H]$ TdR$\}$ uptake into the DNA of the HT-2 indicator cells of that second culture.

This situation mimics the in vivo setting in which an antigen presenting cell is contacted with an effector compound of the present invention in the presence of a second antigenic peptide free in solution. In this in vivo context, the effector compound of the present invention stimulates exchange of the second antigenic peptide for an antigenic peptide bound in the antigen binding groove of MHC class II molecules. Thus, a claim reciting "contacting the above-identified components under physiological conditions" is intended to encompass an application in which an effector compound of the present invention is administered therapeutically to an individual.

The results reported in Examples 1–5 demonstrate that the effector compounds are characterized by the ability to increase interleukin release in the simultaneous assay above the baseline value seen in the response to the antigenic peptide without addition of an effector compound of the present invention. For example, in Table 1, truncated homologs of the peptide YRMKLPKSAKPVSQMR (SEQ ID NO:3) were synthesized, and their biological activity was assayed in in vitro antigenic peptide presentation assays specific for quantitating T cell hybridoma recognition of antigenic peptides presented by the murine $E^d$ and $E^k$ MHC class II alleles. Nearly every N- and C-terminal truncation of the peptide stimulated interleukin release values exceeding the no peptide control values (i.e., values determined in the absence of an effector compound of the present invention in the incubation mixture) in the murine $E^d$ allele experiments. Similar results were observed throughout Examples 1–4 (Tables 1–18). With an exceptional value falling below the no peptide control value, modifications of the peptide YRMKLPKSAKPVSQMR (SEQ ID NO:3) maintained the ability to stimulate interleukin release (at least in a locus-specific manner) in the simultaneous assay which mimics in vivo therapeutic administration of an antigenic peptide together with an effector compound of the present invention.

The specific peptide modifications reported in Table 1 included N-terminal deletions of up to about 7 amino acid residues; C-terminal deletions of up to about 6 amino acid residues; as well as N- and C-terminally protected variations of the N- and C-terminal deletions. Table 2 reports data from N-terminal extension experiments. In this table, data from extensions of up to 6 amino acid residues were reported. Tables 3–10 report data from substitution studies wherein L-amino acid residues in peptides were substituted with other L-isomer amino acids or modified L-isomer amino acids. Table 11–12 report data from studies in which D-isomer amino acids were substituted for selected L-isomer amino acids. Table 13 reports N-methyl amino acid substitution data. Table 14 reports N-methyl substitution data, with some peptides including D-isomer amino acid substitution together with N-methyl substitution in a single peptide. Tables 15–18 relate to multiple substitutions, position 5 substitutions and cyclical analogs.

The remarkable observation made in connection with the many modifications reported in Examples 1–4 (Tables 1–18) is that in very few instances was the stimulated interleukin release observed for the substituted peptides, less than the no peptide control. The substitution of aspartate (D) or glutamate (E) for an amino acid found in a wild-type mammalian Ii sequence represents an exception to this observation which was observed in several experiments. The observed locus and allele specificity is discussed more fully below.

Although, as discussed above, interleukin release in the simultaneous assay is generally elevated above no peptide control with nearly all substituted peptides, certain peptides can be identified through analysis of the data which perform substantially better than others. One of skill in the art would predict with a high degree of certainty that similar screening assays conducted using human, rather than murine MHC class II alleles, would identify effector compounds exhibiting effects similar to those observed in connection with the murine alleles. The identification of such effector compounds is a matter of routine experimentation, given the present disclosure.

The effector compounds of the present invention find application in a variety of in vitro and in vivo therapeutic contexts. Generally, the methods are applied either for the purposes of immunosuppression or antigen supercharging.

Antigen supercharging is accomplished using the effector compounds of the present invention by exploiting both the "antigen spilling" and the "antigenic peptide binding" properties of the compositions discussed above. Antigen spilling refers to the ability of the effector compounds to remove antigenic peptide from the antigenic peptide binding groove of MHC class II molecules on the surface of antigen presenting cells. The antigenic peptide binding property refers to the facilitation (by effector compounds) of the binding of a second peptide with immunomodulatory properties into the antigen peptide binding groove of MHC class II molecules. Thus, effector compounds having the ability to stimulate the ejection of antigenic peptides from MHC class II, are contacted with antigen presenting cells in the presence of a second antigenic peptide. The object of the therapeutic approach is to stimulate the exchange of the second antigenic peptide for the antigenic peptide which is prebound, in vivo, to the antigen peptide binding groove of MHC class II.

As indicated above, the methods of the present invention include both in vitro and in vivo embodiments. In vitro, antigen presenting cells isolated from an individual (e.g., lymphocytes) are treated by incubating the cells in a solution containing appropriate concentrations of an effector compound (characterized by the ability to spill antigenic peptide either in the presence of a second antigenic peptide or in the absence of a second antigenic peptide) together with appropriate concentrations of a second peptide. Again, the goal of the in vitro incubation is to substitute the second peptide for the first peptide in the peptide binding groove of MHC class II molecules on the surface of lymphocytes following stimulation of the ejection of the first peptide. Following treatment of the cells in vitro, they are reinfused into the individual at which time T cells responsive to the second antigenic peptide will be presented with the antigen and an immune response will be stimulated against the second antigenic determinant.

For example, antigen presenting cells originating from a patient can be contacted in vitro with a solution containing a tumor vaccine peptide together with an effector compound of the present invention which aids in the exchange of the tumor vaccine peptide for an antigenic peptide found in association with MHC class II on the surface of the cells originating from the patient. In the case of malignant antigen presenting cells (such as some cells of the lymphoma or melanoma classes of malignancies) such antigenic peptide-primed cells can be rendered incapable of proliferating prior to reinfusion into the patient.

Another application for the effector compounds of the present invention for the enhancement of immunity against cancer determinants, is the in vitro treatment of malignant cells taken from a patient, with an effector compound. The effector compound of the invention, through an action on intracellular processing and binding of endogenous tumor-associated determinants in a malignant cell, enhances binding to the intracellular MHC class II molecules of endogenous tumor-associated determinants prior to their surface expression on the cell. That is, by disrupting the occupancy by Ii or Ii fragments of the antigenic peptide binding site of MHC class II molecules, additional endogenous peptides come to be bound in MHC class II molecules and subsequently presented. In that manner the patient will become primed to both more and a wider range of endogenous tumor-associated determinants than available through current cancer vaccine peptide immunization schemes.

Another use of the effector compounds of the present invention is to enhance in vitro peptide charging of antigen presenting cells for the purpose of developing either cloned T cell lines or of T cell hybridomas, all being of therapeutic or diagnostic value. To this end, the more efficient identification of autoimmune disease-related, antigenic peptides is made possible. In studies by others, antigenic peptides were acid-eluted from immunopurified MHC class II molecules from antigen presenting cells obtained from clinical material. After HPLC separations, some of those peptides were tested for biological activity in vitro. The activities of trace quantities of such peptides can be enhanced greatly by the adjuvant effect of the effector compounds of the present invention.

Related to that use to characterize naturally occurring, disease-related peptides from immunopurified MHC class II molecules is the use of effector compounds to release antigenic peptides, or a subset of antigenic peptides, from such MHC class II molecules.

In vivo, the antigen spilling effector compound is coadministered with the second antigenic peptide at concentrations appropriate for the supercharging of MHC class II molecules on the surface of antigen presenting cells with a second antigenic peptide. The effector compound and the second antigenic peptide can be administered through conventional delivery modes including, for example: intramuscular injection, oral, intranasal or buccal administration, through the use of a subcutaneous implant wherein the release is controlled, or through direct injection into a locally inflamed space (e.g., a joint).

As mentioned above, the present invention relates primarily to two therapeutic modalities—antigen supercharging and immunosuppressant activities. With respect to antigen supercharging, compositions of the present invention can be applied to immunotherapy of allergic disease. For example, immunization with an allergy suppressing peptide, such as those which have been described for the treatment of allergy to ragweed or cat dander, can be enhanced by coinjection in a formulation containing both the allergy suppressing peptide and an effector compound of this invention selected to be effective in augmenting presentation of antigenic peptides by human MHC class II molecules. The effector compound would enhance presentation of the allergy suppressing antigen by a mechanism similar to that which takes place in the simultaneous assays, as reported in the Examples.

Similarly, the effector compounds can be applied in the therapy of malignant disease. For example, immunization with a malignancy-associated peptide, such as a malignant melanoma specific peptide, can be enhanced by coinjection with an effector compound to augment presentation of antigenic peptides by human MHC class II molecules.

In addition to applications related to antigen supercharging, the present invention relates also to immunosuppressant methods. As discussed above in connection with the antigen supercharging embodiments, the immunosuppressant embodiments may be practiced in vitro or in vivo. The formulation and delivery methods are substantially similar for both the immunosuppressant and antigen supercharging embodiments, but for the fact that no second antigenic peptide is included in immunosuppressant embodiments. Rather, the antigen spilling property of the effector compounds are exploited to remove an autodeterminant peptide from the MHC class II antigen peptide binding groove. Immunosuppression is the clinical effect, although the antigenic peptide binding groove might be filled by an ambient peptide.

Effector compounds of the present invention, when found to be effective in certain human MHC class II alleles (with or without relative allele specificity of action) can be applied to the treatment of disease. For example, in the case of autoimmune disease, effector compounds can be administered to affected individuals in a manner appropriate for the suppression of presentation of disease-related antigenic determinants. Such administration might be systemic by oral, intravenous, intramuscular, subcutaneous, intraperitoneal routes, or by local injection, such as into an inflamed joint. Systemic and/or local control of disease can thus be achieved. Such therapeutic control is achieved by contacting the patients' inflammatory or other antigen presenting cells with an effector compound in a manner sufficient to effect the nonstimulating state as revealed in vitro in assays of the Examples. Specific examples of human autoimmune disease suited for therapy include, for example, rheumatoid arthritis, multiple sclerosis, diabetes mellitus, lupus erythematosus and psoriasis.

Certain effector compounds can be applied to suppress allograft rejection. Systemic treatment of antigen presenting cells of an allograft recipient with such compositions, as subsequently chosen to regulate presentation of antigenic peptides by a wide range of human MHC class II molecules, would lead to immunosuppression. Preferred compositions include the cyclical AE381, a cyclical form of the sequence LRMKLPK (SEQ ID NO:4), joined through an amido bond from the N-terminal amino group to the C-terminal carboxyl group of the peptide, and homologs which suppress the antigenic peptide prepulse assay without effecting antigen supercharging in the simultaneous assay.

Selected effector compounds of the present invention were determined to exhibit MHC class II allele-specificity. MHC class II allele-specificity refers to the preferential interaction of compounds of given chemical structures with one MHC class II allele as compared to interaction with a second MHC class II allele at the same genetic locus. The expression "allele-specificity", as used herein, refers to a differential in the simultaneous assay described below, of at least about 2-fold. For example, in Tables 3–10 of Example 2, shown below, particular amino acid substitutions were identified which exhibited a high degree of activity on the $E^d$ allele as compared with the $E^k$ allele. In addition, other modifications were determined to exhibit a high degree of activity on the $E^k$ allele as compared with the $E^d$ allele. Thus, for any given Ii key peptide, one of skill in the art would predict with a high degree of certainty that an allele-specific homolog could be generated through the use of routine experimentation (e.g., amino acid substitution analysis). While these principles have been established in studies with murine MHC class II alleles, it is predictable with a high degree of certainty that such fundamental principles will extend to studies carried out using human alleles.

A high degree of locus specificity was also observed in the studies reported below. For example, in the legend to Table 3, it is stated that no activity was observed in experiments involving the A locus. Furthermore, while not specifically reported herein, in the experiments summarized in Tables 3–10, parallel experiments were conducted with the A locus alleles. In every instance, the compositions of the present invention exhibited less than 15% activity when carried out with A locus alleles, as compared with otherwise identical studies carried out with E locus alleles.

Allele- and locus-specific effector compounds are useful, for example, in connection with in vivo and in vitro therapeutic applications of the type described above. The fact that effector compounds are significantly more active on one, or a few, MHC class II alleles at one genetic locus, as compared with other alleles at that same genetic locus, has therapeutic implications. This is also true with respect to observations of significantly more activity in connection with alleles at one genetic locus, as compared to alleles at a second genetic locus. Such differential activity on one or a few alleles at one genetic locus and/or one genetic locus of MHC class II molecules, leads to a more favorable therapeutic index. The therapeutic index is the ratio of the effective therapeutic dose to the dose at which a significant toxicity is observed. Effector compounds of this invention, being active at only a subset of the MHC class II molecules which are responsible for presentation of antigenic epitopes to the T lymphocytes which regulate the disease process, can regulate that disease process selectively while MHC class II products of other, relatively unaffected alleles or loci remain available to present epitopes from common infectious agents. Many autoimmune diseases which demonstrate familial patterns of inheritance, have been shown to be linked genetically to alleles of the MHC Class II molecules. For example, forms of rheumatoid arthritis are linked to certain alleles of the HLA-DR4 allele of MHC class II molecules. Blocking inflammatory responses through that allele specifically, can be predicted to suppress the inflammatory response while leaving available MHC class II molecules from other alleles and genetic loci for protection against common infections. A significant side effect of current cytotoxic, immunosuppressive therapies for rheumatoid arthritis is generalized immunosuppression (regardless of MHC class II alleles possessed by the patient). Achieving MHC class II allele and/or locus specificity is therefore of considerable clinical value in treating patients with autoimmune disease. Parallel arguments for the value of the specificity of action of effector compounds of this invention can be made for their use in controlling MHC class II allele-related responses to allergens and vaccine peptides.

As disclosed herein, the effector compounds of the present invention are effective in the modulation of the immune response for the purposes either of inducing immunosuppression or of enhancing the immunomodulatory capacity of a second antigenic peptide which is introduced into the MHC class II molecules by the antigen supercharging property of the effector compounds of the invention. The effector compounds of this invention can also be applied to the discovery of an additional class of organic compounds which act by becoming bound into the antigenic peptide binding groove. Such additional compounds are characterized by the ability to bind into a MHC class II molecule with such a tight affinity, as to inactivate the biological function of the MHC class II molecule with potency of a covalent inhibitor. Such compounds are referred to herein as "immunomodulatory organic compounds", to avoid confusion with the "effector compounds" of the invention (which also possess immunomodulatory characteristics).

Screening such immunomodulatory organic compounds using differing MHC class II alleles can identify MHC class II allele specificity. Immunomodulatory organic compounds which exhibit this type of allele specificity can be used to inactivate the biological activity of subsets of MHC class II molecules associated with particular autoimmune or other diseases. Parenthetically, it is noted that although significant degrees of MHC class II allele specificity have been disclosed in the experiments described herein, yet greater degrees of MHC class II allele activity for therapeutic purposes will likely be achieved through the use of the effector compounds of the invention to potentiate the binding (and identification) of this second class of compounds, the immunomodulatory organic compounds.

The immunomodulatory organic compounds are identified by screening collections of organic compounds for their specific binding to MHC class II molecules to which an effector compound of the present invention has been specifically bound, relative to binding to control MHC class II molecules to which no effector compound has been bound. The experiments disclosed herein demonstrate the stable association of certain effector compounds with MHC class II molecules. Such stable complexes demonstrate altered conformations through the increased lability of bound antigenic peptides and the increased facility of binding of second antigenic peptides. Immunomodulatory organic compounds identified by the methods described herein can be used in therapeutic contexts to alter an immune responses. Such compounds would be administered to individuals by systemic or parenteral routes and would contact MHC molecules within those individuals. Alternately, such compounds would be administered in formulations with effector compounds of this invention in a fashion in which the effector compound would, upon contacting a MHC class II molecule on an antigen presenting cell, facilitate the binding of the immunomodulatory organic compound.

EXAMPLES

Example 1

Identification of the shortest, most active AE101 series sequence.

Three in vitro assays of the effects of AE101 series compounds (also referred to as effector compounds) on presentation of antigenic peptides are used in the experiments presented in these Examples. These three assays test in various ways the molecular mechanism of action of the subject compounds. The assays are the "simultaneous assay", the "peptide prepulse assay", and the "processed antigen assay".

In the "simultaneous assay" the four components of the assay are cultured together for a 24 h period. The components of this primary culture, added at the same time or simultaneously, are: (a) the antigenic peptide, (b) mitomycin C-treated, MHC class II-positive antigen presenting cells (APC) with the MHC class II allele required for binding of the specific antigenic peptide and its presentation to the antigenic peptide-specific T cell hybridoma, (c) an AE101 series effector peptide, and (d) MHC class II allele-restricted T cell hybridoma specific for the antigenic peptide and the MHC class II allele restricting its presentation. At the end of the incubation of this primary culture, an aliquot of its supernatant is transferred into a second culture well for incubation with an interleukin-dependent lymphoblastoid cell line. The degree of stimulation of that second, indicator cell by the interleukins which had been released from the activated T cell hybridoma in the primary culture is measured by quantitating tritiated thymidine deoxyribose {[$^3$H] TdR} uptake into the DNA of the HT-2 indicator cells of that second culture.

In a second type of assay, the "peptide prepulse assay", the antigenic peptide is incubated with paraformaldehyde-fixed APC for 6 h. The APC are washed and incubated for 24 h with the AE101 series homolog and the T cell hybridoma specific for the antigenic peptide. After that incubation, an aliquot of the culture supernatant is transferred to a second culture to measure the relative degree of T hybridoma stimulation, as reflected in the effect of released interleukins on the growth of an interleukin-dependent, indicator cell line, as described above.

The two above described assays measure different aspects of the molecular mechanism of the AE101 series of peptides. In the "simultaneous assay", AE101 series peptides are thought to induce the release of endogenously bound peptides and to permit the binding of the second, specific antigenic peptide which is relatively abundant in the culture fluid. The AE101 series peptides enhance antigenic peptide-specific T cell responses in simultaneous assays. In the "peptide prepulse" assay, the specific antigenic peptide becomes bound to MHC class II molecules on the surface of the fixed APC during the 6 h prepulse incubation. The effect of the AE101 series homologs is then thought to release that antigenic peptide, resulting in an apparent suppression of the immune response.

The AE101 series peptides are thought to contact the MHC class II molecules at a discrete site outside the antigenic peptide-binding groove. AE101 peptide binding to this "Ii-KEY" site is thought to induce a conformational change in the MHC class II molecules accelerating the dissociation of previously bound antigenic peptide. The released, specific antigenic peptide is of such low concentration after release that its rebinding is effectively prevented by dilution in the surrounding culture medium. The AE101 series peptides thus inhibit antigenic peptide-specific T cell responses in the "peptide prepulse" assays.

In a third type of assay, the "processed antigen assay", certain of the AE101 series of peptides inhibit stimulation of specific T cell hybridomas by antigenic peptides which are derived from the endogenous processing of a native protein antigen. This assay, which is related to the peptide prepulse assay, is performed by incubating APC with native protein antigen for 8 h, after which the pulsed APC are washed and treated with mitomycin C. Those pulsed APC are then combined with AE101 series peptides and T cell hybridomas and are incubated for 24 h. After that incubation, an aliquot of the culture supernatant is transferred to a second culture to measure T cell stimulation, as reflected in the effect of released interleukins on the growth of an interleukin-dependent, indicator cell line. During the 8 h incubation with native protein antigen, the protein antigen is taken into the APC. The native protein enters the processing pathway within the APC, where it is enzymatically cleaved to peptide fragments. Those peptide fragments with high affinity for the particular MHC class II molecules produced by the APC form antigenic peptide/MHC class II complexes which are transported to the cell surface. At the cell surface, the MHC class II molecules are contacted by the AE101 peptides, which cause the release of the antigenic peptide by the same mechanism proposed for the "peptide prepulse" assay above.

For these various assays, the following antigenic peptides were used: HEL11-25, hen egg lysozyme 11-25, AMKRHGLDNYRGYSL($A^d$) (SEQ ID NO:5); HEL46-61, hen egg lysozyme 46-61, NTDGSTDYGILQINSR($A^k$) (SEQ ID NO:6); HEL106-116, hen egg lysozyme 106-116, NAWVAWRNRCK ($E^d$) (SEQ ID NO:7); PGCC81-104, pigeon cytochrome c 81-104, IFAGIKKKAERADLIAY-LKQATAK ($E^k$) (SEQ ID NO:8); and THMCC82-103, tobacco hornworm moth cytochrome c 82-103, FAGLK-KANERADLIAYLKQATK ($E^k$) (SEQ ID NO:9). AE101 series peptides were obtained from commercial sources. In general, the purity and composition of each peptide was confirmed by HPLC separation and mass spectrometry. The native protein antigens were HEL, hen egg lysozyme, and PGCC, pigeon cytochrome C. They were obtained from commercial sources.

In all assays antigenic peptides and the AE-101 series peptides were dissolved in phosphate-buffered saline (PBS; 0.01M sodium phosphate buffer, pH 7.2, 0.1M NaCl). The solutions were sterilized by filtration, and the peptide concentrations were determined by amino acid analysis (Applier Biosystems, Inc. 420A/130A derivatizer/HPLC after hydrolysis with 6N HCl for 24 h in vacuo).

For the experiments of these Examples, several T cell hybridomas, which are specific for certain antigenic peptides, were used. The TPc9.1 T hybridoma is specific for pigeon cytochrome C 81-104 peptide presented on the murine class II MHC allele $E^k$. The TPc9.1 hybridoma responds heteroclitically to tobacco hornworm moth cytochrome c 82-103 on $E^k$. The 3A9 T hybridoma is specific for hen egg lysozyme 46-61 on $A^k$. The 9.30. B2 hybridoma is specific for hen egg lysozyme 11-25 on $A^d$, and the G28. C9 hybridoma is specific for hen egg lysozyme 106-116 on $E^d$. The A20 and CH27 B cell lymphoma lines express H-$2^d$ and H-$2^k$ alleles, respectively.

Antigenic peptide-specific T cell activation was measured by the following procedure. Mitomycin C-treated A20 cells ($A^dE^d$) or CH27 cells APC ($A^kE^k$) were generated by incubating 5×10$^6$ cells/mL for 20 min at 37° C. with 0.025 mg/mL of mitomycin C (Sigma) in Dulbecco's Modified Eagle's Medium (DMEM)/10 mM N-2 (hydroxyethylpiperazine-N"[2-ethanesulfonic acid]

(HEPES), followed by two washes with four volumes of DMEM-5% fetal calf serum (FCS), 10 mM HEPES. Fixed APC were generated by treating $1 \times 10^6$ cells/mL for 5 min with 0.5% paraformaldehyde in PBS (pH 7.2), followed by two washes with four volumes of DMEM-10% FCS, 10 mM HEPES. T cell hybridomas were irradiated 2200 rads before each assay.

For the "simultaneous assay", $5 \times 10^4$ mitomycin C-treated APC, $5 \times 10^4$ T hybridoma cells and a submaximal concentration of antigenic peptide were cultured with and without serial 4-fold dilutions of each AE101 series peptide, usually at 64 μM, 16 μM, 4 μM, and 1 μM, at pH 7.2–7.4, in complete DMEM-5% FCS, 10 mM HEPES, 1× nonessential amino acids (Sigma), 1 mM sodium pyruvate, 2 mM L-glutamine, 100 U/mL penicillin G, 100 μg/mL streptomycin sulfate, $5 \times 10^{-5}$ M 2-mercaptoethanol (2-ME). Wells containing only T hybridoma cells (T)+APC were included to monitor for background T cell activation; and wells containing T+APC+AE101 series peptide were included to monitor for non-specific T hybridoma activation by each AE101 series peptide. Supernatants (aliquots of 20, 40 or 75 μl) from each culture were removed after 24 h and were assayed for their effect on growth of $1 \times 10^4$ interleukin-dependent HT-2 lymphoblastoid cells (added in 140, 120 or 75 μl complete Roswell Park Memorial Institute (RPMI) 1640 buffer—5% FCS, respectively), as measured by incorporation of [$^3$H]TdR, added at 1 μCi/well during the last 5 h of a 24 h HT-2 assay. For all assays the reported value is the mean of triplicate wells, with a mean standard error of less than±10%. Since the degree of stimulation varied among assays, usually both in the primary culture and in the secondary HT-2 indicator culture, for comparisons among assays performed at different times, standard or reference peptides were always included.

The "peptide prepulse assay" was carried out under essentially the same conditions as described for the "simultaneous assay" with the following modifications. Fixed APC were first incubated for 6 h at $1 \times 10^6$ cells/mL in complete DMEM-5% FCS in 24-well microculture plates (1 mL/well) with antigenic peptide, followed by four washes with 10 volumes of DMEM-5% FCS. The cells were then exposed to varying concentrations of AE10 series peptide (64 μM, 16 μM, 4 μM, and 1 μM) for 24 h in the presence of the T cell hybridoma specific to the antigenic peptide. Interleukin release from these cultures was measured by proliferation of HT-2 cells to interleukins in supernatants transferred from the primary culture. Generally, a single dose of 64 μM of each AE101 series peptide was used. The baseline T cell response was measured by culturing T hybridoma cells with the antigenic peptide-prepulsed APC in the absence of AE10 series peptides.

The "processed antigen assay" was carried out under essentially the same conditions as the "peptide prepulse assay", with the following modifications. Untreated APC were incubated at $1 \times 10^6$/mL in 24-well plates (1 mL/well) with native protein antigen for 8 h. Following that incubation, the pulsed APC were washed, treated with mitomycin C, and washed again. AE101 series peptide was added at 64 μM, 16 μM, 4 μM, and 1 μM concentrations for 24 h in the presence of the T cell hybridoma specific for the antigenic peptide. Interleukin release from these cultures was measured by proliferation of HT-2 cells to interleukins in supernatants transferred from the primary culture. The baseline T cell response was measured by culturing T hybridoma cells with the native antigen-prepulsed APC in the absence of AE101 series peptides.

In order to define the shortest AE101 series peptide with the maximal activity, a series of N- and C-terminally truncated homologs of AE101 was synthesized (Table 1). The biological activities of these peptides were assayed in in vitro antigenic peptide presentation assays specific for quantitating T cell hybridoma recognition of certain antigenic peptides presented by the murine $E^d$ and $E^k$ MHC class II alleles. The assays used were (1) the "simultaneous assay", and (2) the "peptide prepulse assay".

TABLE 1

N- and C-Terminal Truncation Analogs of AE101.

| Peptide | Sequence | $E^d$ | $E^k$ |
|---|---|---|---|
| None | | 1.0 | 1.0 |
| AE101 | YRMKLPKSAKPVSQMR (SEQ ID NO:3) | 13.6, 4.9 | 1.0, 0.8 |
| AE102 | RMKLPKSAKPVSQMR (SEQ ID NO:10) | 13.3, 4.2 | 1.0, 0.8 |
| AE103 | KLPKSAKPVSQMR (SEQ ID NO:11) | 3.4, 1.3 | 0.7, 0.7 |
| AE104 | PKSAKPVSQMR (SEQ ID NO:12) | 2.6, 0.9 | 0.8, 1.1 |
| AE105 | SAKPVSQMR (SEQ ID NO:13) | 4.5, 1.1 | 0.7, 0.8 |
| AE106 | YRMKLPKSAKPVSQ (SEQ ID NO:14) | 16.9, 4.4 | 2.0, 0.9 |
| AE107 | YRMKLPKSAKPV (SEQ ID NO:15) | 21.7, 4.8 | 1.0, 0.8 |
| AE108 | YRMKLPKSAK (SEQ ID NO:16) | 32.0, 11.6 | 1.2, 0.9 |
| AE109 | Ac-YRMKLPKSAK-NH$_2$ (SEQ ID NO:16) | 39.3, 20.8 | 6.9, 2.2 |
| AE110 | Ac-LRMKLPKSAK-NH$_2$ (SEQ ID NO:17) | 47.1, 27.8 | 7.6, 2.1 |
| AE167 | Ac-LRMKLPKPPP-NH$_2$ (SEQ ID NO:18) | 20.1, n.d. | 3.4, n.d. |
| AE168 | Ac-LRMKLPKPPK-NH$_2$ (SEQ ID NO:19) | 16.7, n.d. | 4.7, n.d. |
| AE111 | Ac-YRMKLPKSA-NH$_2$ (SEQ ID NO:20) | 39.2, 18.8 | 7.2, 2.0 |
| AE112 | Ac-YRMKLPKS-NH$_2$ (SEQ ID NO:21) | 42.8, 26.2 | 15.3, 3.2 |
| AE113 | Ac-YRMKLPK-NH$_2$ (SEQ ID NO:22) | 36.3, 23.1 | 15.5, 6.7 |
| AE114 | Ac-LRMKLPK-NH$_2$ (SEQ ID NO:23) | 39.8, 26.0 | 15.9, 3.9 |
| AE115 | Ac-YRMKLP-NH$_2$ (SEQ ID NO:24) | 19.9, 5.7 | 18.6, 3.8 |
| AE116 | Ac-YRMKL-NH$_2$ (SEQ ID NO:25) | 7.1, 2.1 | 15.5, 3.2 |
| AE117 | Ac-YRMK-NH$_2$ (SEQ ID NO:26) | 2.3, 1.0 | 14.6, 10.6 |
| AE118 | Ac-YRM-NH$_2$ (SEQ ID NO:27) | 1.0, 0.6 | 5.6, 3.0 |

Table 1: Activities of N- and C-terminal truncation analogs of AE101 peptide in a simultaneous assay. Activities for each allele are given as "Times Baseline Response" for assays with the $E^d$ and $E^k$ alleles. For this simultaneous assay, MHC class II-positive APC, treated with mitomycin C, were incubated with an antigenic peptide-specific T cell hybridoma, the respective antigenic peptide, and an AE101 series peptide. The concentrations of antigenic (Ag) peptides were 0.4 μM of HEL106-116 for $E^d$ and 0.075 μM of THMCC82-103 for $E^k$. The AE101 series peptides were used at 64 μM (first value) and 16 μM (second value) for $E^d$ and $E^k$. Interleukin released from the T hybridoma cells was quantitated after 24 h by [$^3$H]TdR incorporation in interleukin dependent HT-2 cells. The dilutions of primary culture supernatant taken into the HT-2 cell assay were 1:4 for $E^d$ and 1:2 for $E^k$. The observed response, "Times Baseline Response", equaled CPM of (T+APC+Ag peptide+AE101 series peptide)/CPM of (T+APC+Ag peptide). The means of triplicate wells had an average SEM of ≦10%. The T cell response to antigenic peptide alone was designated as the baseline value 1. "No peptide" was an assay without AE101 series peptide. The single letter amino acid codes used throughout all Tables are as follows: A=L-alanine, Cit=L-citrulline, D=L-aspartate, E=L-glutamate, F=L-phenylalanine, H=L-histidine, Harg=L-homoarginine, K=L-lysine, k=D-lysine, L=L-leucine, l=D-leucine, mL=n-methyl-L-leucine, M=L-methionine, m=D-methionine, N=L-asparagine, Orn=L-ornithine, P=L-proline, p=D-proline, hydrP=L-hydroxyproline, R=L-arginine, r=D-arginine, Q=L-glutamine, and Y=L-tyrosine. Whenever mL appears in a table, it is set off by brackets to lessen confusion with "D-methionine, L-Leucine". Likewise, whenever Harg, Cit, Orn occur in a table, they are set off by spaces to lessen confusion, for example, with "L-histidine, D-alanine, D-arginine, D-glycine" etc.

These assays revealed the activity of the AE114 peptide which contained the 7 amino acid primary sequence of murine Ii76-91 and human Ii77-92, respectively (sequences in both species being identical), with N-terminal acetylation and C-terminal amidation. While AE114 is active on both the murine class II MHC $E^d$ and $E^k$ alleles, the shorter tetrapeptide AE117 retained full activity on $E^k$ but not on $E^d$. For the $E^d$ allele, the shortest peptide analog retaining the maximal observed activity was the 7-mer, AE114. Replacing the N-terminal tyrosine (Y) by leucine (L; the wild type residue) slightly increased the potency of the peptide in the $E^d$ system (AE110>AE109, and AE114>AE113). Blocking the N- and C-termini increased the potency of the AE108 peptide in both the $E^d$ and $E^k$ systems: AE109>AE108.

TABLE 2

N-Terminal Extension Analogs of AE110.

| Peptide | Sequence | $E^d$ | $E^k$ | $A^d$ | $A^k$ |
|---|---|---|---|---|---|
| None | | 1.0 | 1.0 | 1.0 | 1.0 |
| AE109 | Ac-YRMKLPKSAK-NH$_2$ (SEQ ID NO:16) | 25.5 | 43.7 | 0.9 | 1.2 |
| AE110 | Ac-LRMKLPKSAK-NH$_2$ (SEQ ID NO:17) | 23.8 | 19.1 | 0.7 | 0.8 |
| AE155 | Ac-SLRMKLPKSAK-NH$_2$ (SEQ ID NO:28) | 23.4 | 8.4 | 0.8 | 1.0 |
| AE154 | Ac-DSLRMKLPKSAK-NH$_2$ (SEQ ID NO:29) | 15.1 | 2.2 | 1.1 | 1.0 |
| AE153 | Ac-LDSLRMKLPKSAK-NH$_2$ (SEQ ID NO:30) | 8.5 | 1.4 | 1.2 | 1.0 |
| AE152 | Ac-QLDSLRMKLPKSAK-NH$_2$ (SEQ ID NO:31) | 2.3 | 0.4 | 0.9 | 0.5 |
| AE151 | Ac-LQLDSLRMKLPKSAK-NH$_2$ (SEQ ID NO:32) | 2.5 | 0.6 | 1.1 | 0.5 |
| AE150 | Ac-NLQLDSLRMKLPKSAK-NH$_2$ (SEQ ID NO:33) | 3.2 | 0.8 | 1.0 | 0.0 |

Table 2: Activities of N-terminally extended AE101 series peptides in a simultaneous assay. Activities (Time Baseline Response) for enhancement of antigen presentation for each indicated allele were determined in a simultaneous assay carried out as described in the legend of Table 1, with the following modifications. The concentrations of antigenic peptides were 0.05 μM of HEL46-61 for $A^k$ and 0.05 μM of HEL11-25 for $A^d$. The concentrations of antigenic peptides were 0.05 μM of PGCC81-104 for $E^k$ and 0.05 μM of HEL106-116 for $E^d$. The concentration of AE101 series peptides was 64 μM in all four allelic systems. A 1:2 dilution of supernatant of the primary culture was taken for the HT-2 cell assays for all four allelic systems. The N-terminal extensions in peptides AE150 through AE155 are wild-type residues from positions from $N^{70}$ to $S^{75}$ in the amino acid sequence of murine Ii.

In the $E^d$ and $E^k$ allelic systems, extending the N-terminus of the AE110 peptide with additional wild-type sequence of murine Ii resulted in a systematic decrease in the enhancing activity in the "simultaneous" type of assay. In the $E^k$ system in particular, such N-terminal extension finally led to inhibition (AE152 and AE151). In the $A^d$ system, while AE110 was not active, such N-terminal extensions also "uncovered" no activity. In the $A^k$ system, where the AE110 reference peptide was inactive, addition of N-terminal wild-type sequence led to inhibitory peptides: AE152, AE151, and AE150.

In summary, the experiments of this Example demonstrate the shortest active AE101 series peptides, acceptance in an in vitro assay of N- and C-terminal protection against exopeptidases, and significant MHC Class II allele specificity of certain peptides as a function of peptide length.

Example 2

L-Isomer amino acid substitutions at 5 positions in AE114 and 2 positions in AE109 (a longer analog of AE114) indicate side chain preferences for potency and for allele-specificity.

Amino acid substitutions at 5 positions in AE114 (a 7-amino acid peptide) and 2 positions in AE109 (a 10-amino acid peptide) defined preferences for certain side chain structures at each of those positions.

TABLE 3

Substitution Series At Leucine[76] (Position 1) in AE114.

| Peptide | Sequence | $E^d$ | $E^k$ |
|---|---|---|---|
| None | | 1.0 | 1.0 |
| AE114 | Ac-L RMKLPK-NH$_2$ (SEQ ID NO:23) | 10.0 | 26.9 |
| AE180 | Ac-Orn RMKLPK-NH$_2$ (SEQ ID NO:34) | 12.6 | 10.8 |
| AE181 | Ac-Cit RMKLPK-NH$_2$ (SEQ ID NO:35) | 9.0 | 11.5 |
| AE182 | Ac-HArg RMKLPK-NH$_2$ (SEQ ID NO:36) | 18.8 | 26.5 |
| AE183 | Ac-H RMKLPK-NH$_2$ (SEQ ID NO:37) | 10.3 | 17.3 |
| AE184 | Ac-K RMKLPK-NH$_2$ (SEQ ID NO:38) | 14.1 | 11.8 |
| AE185 | Ac-D RMKLPK-NH$_2$ (SEQ ID NO:39) | 1.2 | 0.9 |
| AE186 | Ac-E RMKLPK-NH$_2$ (SEQ ID NO:40) | 2.5 | 1.3 |
| AE187 | Ac-N RMKLPK-NH$_2$ (SEQ ID NO:41) | 6.3 | 9.5 |
| AE188 | Ac-Q RMKLPK-NH$_2$ (SEQ ID NO:42) | 8.8 | 7.7 |
| AE189 | Ac-F RMKLPK-NH$_2$ (SEQ ID NO:43) | 12.1 | 18.2 |
| AE113 | Ac-Y RMKLPK-NH$_2$ (SEQ ID NO:22) | 12.3 | 24.9 |
| AE190 | Ac-M RMKLPK-NH$_2$ (SEQ ID NO:44) | 9.8 | 15.2 |

Table 3. Activities of substitution series at Leucine[76] in AE114 in a simultaneous assay. The data are from assays (described in Example 1) in which the concentrations of AE101 series peptide was 64 μM for each allele. The supernatant dilution taken into the HT-2 cell assay was 1:4 for each allele. To compare results between the two systems more easily, the values for the 64 μM AE101 series peptide in the $E^k$ system were reduced relative to the $E^d$ system by a factor of 10, since the baseline CPM for $E^k$ was approximately 0.1 times the baseline CPM for $E^d$.

In the $E^d$ allele, AE114 homologs with HArg, K, Orn, Y, and F at the first position generated peptides with high activities. The least activity was found in homologs with negatively charged residues D and E at that position. In the $E^k$ system, the five amino acid substitutions at the first position in AE114 with high activities were L, HARG, Y, F, and H. The two substitutions with least activity in the $E^k$ system were D and E.

TABLE 4

Substitution Series At Arginine[77] (Position 2) in AE109.

| Peptide | Sequence | $E^d$ | $E^k$ |
|---|---|---|---|
| None | | 1.0 | 1.0 |
| AE109 | Ac-Y R MKLPKSAK-NH$_2$ (SEQ ID NO:16) | 3.3 | 2.3 |
| AE121 | Ac-Y A MKLPKSAK-NH$_2$ (SEQ ID NO:45) | 1.1 | 1.0 |
| AE130 | Ac-Y Orn MKLPKSAK-NH$_2$ (SEQ ID NO:46) | 0.9 | 1.1 |
| AE131 | Ac-Y Cit MKLPKSAK-NH$_2$ (SEQ ID NO:47) | 2.8 | 0.8 |
| AE132 | Ac-Y HArg MKLPKSAK-NH$_2$ (SEQ ID NO:48) | 1.8 | 5.5 |
| AE133 | AC-Y H MKLPKSAK-NH$_2$ (SEQ ID NO:49) | 0.9 | 0.8 |
| AE134 | Ac-Y K MKLPKSAK-NH$_2$ (SEQ ID NO:50) | 0.7 | 0.9 |
| AE135 | Ac-Y D MKLPKSAK-NH$_2$ (SEQ ID NO:51) | 1.2 | 1.0 |
| AE136 | Ac-Y E MKLPKSAK-NH$_2$ (SEQ ID NO:52) | 0.9 | 0.7 |
| AE137 | Ac-Y N MKLPKSAK-NH$_2$ (SEQ ID NO:53) | 0.8 | 0.7 |
| AE138 | Ac-Y Q MKLPKSAK-NH$_2$ (SEQ ID NO:54) | 0.7 | 0.8 |
| AE139 | Ac-Y F MKLPKSAK-NH$_2$ (SEQ ID NO:55) | 0.8 | 1.5 |
| AE140 | Ac-Y Y MKLPKSAK-NH$_2$ (SEQ ID NO:56) | 0.7 | 0.9 |
| AE141 | Ac-Y M MKLPKSAK-NH$_2$ (SEQ ID NO:57) | 1.1 | 1.3 |
| AE142 | Ac-Y L MKLPKSAK-NH$_2$ (SEQ ID NO:58) | 0.8 | 1.0 |

Table 4. Activities of substitution series at Arginine[77] in AE109 in a simultaneous assay. In this assay (as described in Example 1), the concentration of each AE109 homolog was 64 $\mu$M. The supernatant dilutions taken into the HT2 assays were 1:2 each allele.

In the $E^d$ allele, the following four amino acids at the second position in AE114, where the wild-type amino acid is arginine (R), generated peptides with high activity: Arg, Cit, HArg, and Leu. The two amino acid substitutions which resulted in peptides with least activity were D and E. In the $E^k$ system, the following three amino acids at the second position in AE114 generated highly-active peptides: HArg, lysine, and ornithine. The two replacements in the $E^k$ system resulting in the least active peptides were D and E.

TABLE 5

Substitution Series At Methionine[78] (Position 3) in AE114.

| Peptide | Sequence | $E^d$ | $E^k$ |
|---|---|---|---|
| None | | 1.0 | 1.0 |
| AE114 | Ac-LR M KLPK-NH$_2$ (SEQ ID NO:23) | 10.0 | 26.9 |
| AE195 | Ac-LR Orn KLPK-NH$_2$ (SEQ ID NO:59) | 12.1 | 12.1 |
| AE196 | Ac-LR Cit KLPK-NH$_2$ (SEQ ID NO:60) | 13.6 | 18.4 |
| AE197 | Ac-LR HArg KLPK-NH$_2$ (SEQ ID NO:61) | 10.7 | 39.9 |
| AE198 | Ac-LR H KLPK-NH$_2$ (SEQ ID NO:62) | 16.1 | 18.7 |
| AE199 | Ac-LR K KLPK-NH$_2$ (SEQ ID NO:63) | 12.1 | 22.9 |
| AE200 | Ac-LR D KLPK-NH$_2$ (SEQ ID NO:64) | 8.3 | 3.9 |
| AE201 | Ac-LR E KLPK-NH$_2$ (SEQ ID NO:65) | 7.0 | 3.4 |
| AE202 | Ac-LR N KLPK-NH$_2$ (SEQ ID NO:66) | 18.2 | 9.3 |
| AE203 | Ac-LR Q KLPK-NH$_2$ (SEQ ID NO:67) | 14.1 | 20.5 |
| AE204 | Ac-LR F KLPK-NH$_2$ (SEQ ID NO:68) | 14.0 | 31.8 |
| AE205 | Ac-LR Y KLPK-NH$_2$ (SEQ ID NO:69) | 13.9 | 27.4 |
| AE206 | Ac-LR L KLPK-NH$_2$ (SEQ ID NO:70) | 11.9 | 33.9 |

Table 5: Activities of substitution series at Methionine[78] in AE114 in a simultaneous assay. In this assay (as described in Example 1), the concentration of the AE101 series peptide was 64 $\mu$M. The supernatant dilution taken into the HT-2 cell assay was 1:4 for each allele. The AE101 series peptide effects in the $E^k$ system were normalized to the $E^d$ system by a factor of 10 since the baseline CPM for $E^k$ was approximately 0.1 times the baseline CPM for $E^d$.

In the $E^d$ allelic system, the following six amino acids at the third position in AE114, where the wild-type amino acid is methionine (M), generated peptides with high activity: N, H, Q, F, Y, and Cit. The two amino acid substitutions with the least activity were residues D and E.

In the $E^k$ system, the following seven amino acids at the third position in AE114 generated highly-active peptides were: Arg, HArg, L, F, Y, M, K, and Q. The two replacements in the $E^k$ system resulting in the least active peptides were D and E.

TABLE 6

Substitution Series At Lysine[79] (Position 4) in AE114.

| Peptide | Sequence | $E^d$ | $E^k$ |
|---|---|---|---|
| No peptide | | 1.0 | 1.0 |
| AE114 | Ac-LRM K LPK-NH$_2$ (SEQ ID NO:23) | 10.6 | 10.7 |
| AE210 | Ac-LRM Orn LPK-NH$_2$ (SEQ ID NO:71) | 6.6 | 9.0 |
| AE211 | Ac-LRM Cit LPK-NH$_2$ (SEQ ID NO:72) | 1.7 | 3.4 |
| AE212 | Ac-LRM HArg LPK-NH$_2$ (SEQ ID NO:73) | 13.2 | 15.4 |
| AE213 | Ac-LRM H LPK-NH$_2$ (SEQ ID NO:74) | 6.1 | 5.7 |
| AE214 | Ac-LRM D LPK-NH$_2$ (SEQ ID NO:75) | 0.8 | 0.4 |
| AE215 | Ac-LRM E LPK-NH$_2$ (SEQ ID NO:76) | 0.7 | 0.4 |
| AE216 | Ac-LRM N LPK-NH$_2$ (SEQ ID NO:77) | 2.4 | 3.3 |
| AE217 | Ac-LRM Q LPK-NH$_2$ (SEQ ID NO:78) | 4.0 | 4.4 |
| AE218 | Ac-LRM F LPK-NH$_2$ (SEQ ID NO:79) | 3.1 | 9.0 |
| AE219 | Ac-LRM Y LPK-NH$_2$ (SEQ ID NO:80) | 7.1 | 8.8 |
| AE220 | Ac-LRM M LPK-NH$_2$ (SEQ ID NO:81) | 2.8 | 12.5 |

Table 6. Activities of substitution series at Lysine[79] in a simultaneous assay. In this assay (as described in Example 1) the concentration of the AE101 series peptides was 64 μM.

The supernatant dilution taken into the HT-2 cell assay was 1:4 for each allele. The AE101 series peptide effects in the $E^k$ system were normalized to the $E^d$ system through reduction by a factor of 5, since the baseline CPM for $E^k$ was approximately 0.2 time the baseline for $E^d$.

In the $E^d$ allelic system, the following six amino acids at the fourth position in AE114, where the wild-type amino acid is lysine (K), generated peptides with high activity:

Met, HArg, K, Y, Orn, and H. The two amino acid substitutions in peptides with the least activity were D and E. In the $E^k$ system, the following five amino acids at the fourth position in AE114 generated peptides with high activities: HArg, M, K, Orn, and F. The two replacements in the $E^k$ system resulting in the least active peptides were D and E.

TABLE 7

Substitution Series At Leucine[80] (Position 5) in AE114.

| Peptide | Sequence | $E^d$ | $E^k$ |
|---|---|---|---|
| No peptide | | 1.0 | 1.0 |
| AE114 | Ac-LRMK L PK-$NH_2$ (SEQ ID NO:23) | 10.6 | 10.7 |
| AE225 | Ac-LRMK Orn PK-$NH_2$ (SEQ ID NO:82) | 10.4 | 13.9 |
| AE226 | Ac-LRMK Cit PK-$NH_2$ (SEQ ID NO:83) | 9.0 | 9.0 |
| AE227 | Ac-LRMK HArg PK-$NH_2$ (SEQ ID NO:84) | 8.1 | 20.5 |
| AE228 | Ac-LRMK H PK-$NH_2$ (SEQ ID NO:85) | 8.5 | 20.3 |
| AE229 | Ac-LRMK K PK-$NH_2$ (SEQ ID NO:86) | 13.2 | 16.2 |
| AE230 | Ac-LRMK D PK-$NH_2$ (SEQ ID NO:87) | 0.6 | 1.1 |
| AE231 | Ac-LRMK E PK-$NH_2$ (SEQ ID NO:88) | 1.8 | 1.2 |
| AE232 | Ac-LRMK N PK-$NH_2$ (SEQ ID NO:89) | 12.5 | 8.9 |
| AE233 | Ac-LRMK Q PK-$NH_2$ (SEQ ID NO:90) | 11.5 | 17.0 |
| AE234 | Ac-LRMK F PK-$NH_2$ (SEQ ID NO:91) | 14.2 | 16.6 |
| AE235 | Ac-LRMK Y PK-$NH_2$ (SEQ ID NO:92) | 14.6 | 21.8 |
| AE236 | Ac-LRMK M PK-$NH_2$ (SEQ ID NO:93) | 15.2 | 16.9 |

Table 7. Activities in substitution series at Leucine[80] in a simultaneous assay. In this assay (described in Example 1), the concentration of the AE101 series peptides was 64 μM. The supernatant dilution taken into the HT-2 cell assay was 1:4 for each allelic systems. The AE101 series peptide effects in the $E^k$ system for 64 μM of AE peptide were normalized to the $E^d$ system by a factor of 5, since the baseline CPM for $E^k$ was approximately 0.2 times the baseline CPM for $E^d$.

For $E^d$, the following five amino acids at the fifth position in AE114, where the wild-type amino acid is leucine (L), generated peptides with high activity: M, Y, F, K, and N. The two amino acid substitutions with the least activity were D and E. In the $E^k$ system, the following five amino acids at the fifth position in AE114 generated peptides with high activities: Y, HArg, H, Q, and M. The two replacements in the $E^k$ system with least activity were D and E.

TABLE 8

Substitution Series At Proline[81] (Position 6) in AE109.

| Peptide | Sequence | $E^d$ | $E^k$ |
|---|---|---|---|
| None | | 1.0 | 1.0 |
| AE109 | Ac-YRMKL P KSAK-$NH_2$ (SEQ ID NO:16) | 16.4, 17.6, 7.4 | 4.3, 1.5, 1.0 |
| AE143 | Ac-YRMKL hydrP KSAK-$NH_2$ (SEQ ID NO:94) | 19.4, 19.6, 8.0 | 4.2, 1.5, 0.98 |

Table 8: Activities of hydroxyproline substitution series at Proline[81]. These data were generated in a simultaneous assay as described in Example 1. The concentrations of AE101 series peptides used in these assays were 64 μM (first), 16 μM (second), and 4 μM (third) for both the $E^d$ and the $E^k$ systems. The supernatant dilutions taken into in the HT-2 cell assay were 1:8 for $E^d$ and 1:4 for $E^k$.

In both the $E^d$ and $E^k$ systems, replacing proline at the sixth position of AE109 with hydroxyproline generated a peptide with equal or greater activity than the peptide with the wild-type sequence.

TABLE 9

Substitution Series At Lysine[82] (Position 7) in AE114.

| Peptide | Sequence | $E^d$ | $E^k$ |
|---|---|---|---|
| None | | 1.0 | 1.0 |
| AE114 | AC-LRMKLP K-$NH_2$ (SEQ ID NO:23) | 7.7 | 13.2 |
| AE240 | Ac-LRMKLP Orn-$NH_2$ (SEQ ID NO:95) | 9.8 | 11.5 |
| AE241 | Ac-LRMKLP Cit-$NH_2$ (SEQ ID NO:96) | 3.4 | 12.2 |
| AE242 | Ac-LRMKLP HArg-$NH_2$ (SEQ ID NO:97) | 8.0 | 17.6 |
| AE243 | Ac-LRMKLP H-$NH_2$ (SEQ ID NO:98) | 7.2 | 14.5 |
| AE244 | Ac-LRMKLP D-$NH_2$ (SEQ ID NO:99) | 0.9 | 2.7 |
| AE245 | Ac-LRMKLP E-$NH_2$ (SEQ ID NO:100) | 0.9 | 2.8 |
| AE246 | Ac-LRMKLP N-$NH_2$ (SEQ ID NO:101) | 7.3 | 16.4 |
| AE247 | Ac-LRMKLP Q-$NH_2$ (SEQ ID NO:102) | 4.5 | 10.9 |
| AE248 | Ac-LRMKLP F-$NH_2$ (SEQ ID NO:103) | 17.2 | 16.3 |
| AE249 | Ac-LRMKLP Y-$NH_2$ (SEQ ID NO:104) | 12.2 | 17.1 |
| AE250 | Ac-LRMKLP M-$NH_2$ (SEQ ID NO:105) | 13.9 | 21.3 |
| AE251 | Ac-LRMKLP L-$NH_2$ (SEQ ID NO:106) | 11.9 | 18.6 |

Table 9: Activities of substitution series at Lysine[82] in a simultaneous assay. In this assay (as described in Example 1), the concentration of AE peptides was 64 μM. The supernatant dilution taken into the, HT-2 cell assay was 1:4 for each allelic system. The AE101 series peptide effect in the $E^k$ system for 64 μM of AE peptide was normalized to the $E^d$ system by a factor of 5, since the baseline CPM for $E^k$ was approximately 0.2 times the baseline CPM for $E^d$.

In the $E^d$ allelic system, the following five amino acids at the seventh position in AE114, where the wild-type amino acid is lysine (K), generated peptides with high activity: F, M, Y, L, and Orn. The two amino acid substitutions which resulted in peptides with the least activity were D and E. In the $E^k$ system, the following six amino acids at the seventh position in AE114 generated peptides with high activities: M, L, HArg, Y, N, and F. The two replacements in the $E^k$ system with least activity were D and E.

TABLE 10

Alanine Scanning Analogs of AE101.

| Peptide | Sequence | $E^d$ | $E^k$ |
|---|---|---|---|
| None | | 1.0 | 1.0 |
| AE120 | Ac-ARMKLPKSAK-NH$_2$ (SEQ ID NO:107) | 35.4, 18.1 | 36.8, 34.9 |
| AE121 | Ac-YAMKLPKSAK-NH$_2$ (SEQ ID NO:108) | 2.7, 1.9 | 21.6, 19.7 |
| AE122 | Ac-YRAKLPKSAK-NH$_2$ (SEQ ID NO:109) | 16.2, 9.2 | 46.2, 41.4 |
| AE123 | Ac-YRMALPKSAK-NH$_2$ (SEQ ID NO:110) | 24.0, 10.7 | 65.0, 51.1 |
| AE124 | Ac-YRMKAPKSAK-NH$_2$ (SEQ ID NO:111) | 12.5, 7.3 | 66.0, 65.9 |
| AE125 | Ac-YRMKLAKSAK-NH$_2$ (SEQ ID NO:112) | 2.0, 1.7 | 38.7, 32.8 |
| AE126 | Ac-YRMKLPASAK-NH$_2$ (SEQ ID NO:113) | 18.2, 6.8 | 53.4, 56.4 |
| AE127 | Ac-YRMKLPKAAK-NH$_2$ (SEQ ID NO:114) | 19.1, 12.4 | 63.6, 63.4 |
| AE109 | Ac-YRMKLPKSAK-NH$_2$ (SEQ ID NO:16) | 27.5, 24.3 | 66.0, 56.3 |
| AE128 | Ac-YRMKLPKSAA-NH$_2$ (SEQ ID NO:115) | 33.0, 29.5 | 51.9, 58.6 |

Table 10: Activities of alanine substitution analogs of AE109 in a simultaneous assay. In this assay (as described in Example 1), the concentrations of AE101 series peptides were 64 $\mu$M (first value) and 16 $\mu$M (second value) for $E^d$ and 64 $\mu$M (both values) for $E^k$. AE109 has the wild-type sequence, with alanine in the ninth position. The supernatant dilution taken into the HT-2 cell assay was 1:2 for $E^d$ and 1:2 (first value) and 1:4 (second value) for $E^k$.

Substituting alanine (A) for arginine (R) at the second position and for proline (P) at the sixth position in AE109 generated peptides with significantly decreased enhancement in the simultaneous assay. These two positions define two pharmacophores, i.e., side chains which are critical for peptide activity.

Example 3

Certain D-amino acid substitutions lead to backbone-protected homologs retaining partial activity.

The activity of the AE101 series peptide in the in vitro T cell functional assays is dependent on at least two factors: binding to the drug's active site on MHC class II molecules and the half-life of the peptide during the co-culture. In order to design more stable AE101 series compounds, a series of analogs with single, systematic D-isomer substitutions at each residue position was synthesized ("the D-scan series"). Incorporating D-amino acids would presumably render such peptides more resistant to cleavage by proteases about the D-amino acid-substituted residue position.

TABLE 11

D amino acid scanning analogs of AE114.

| Peptide | Sequence | $E^d$ | $E^k$ |
|---|---|---|---|
| None | | 1.0 | 1.0 |
| AE114 | Ac-LRMKLPK-NH$_2$ (SEQ ID NO:23) | 24.1 | 5.2 |

TABLE 11-continued

D amino acid scanning analogs of AE114.

| Peptide | Sequence | $E^d$ | $E^k$ |
|---|---|---|---|
| AE160 | Ac-l RMKLPK-NH$_2$ (SEQ ID NO:116) | 11.0 | 1.7 |
| AE161 | Ac-L r MKLPK-NH$_2$ (SEQ ID NO:117) | 4.0 | 1.1 |
| AE162 | Ac-LR m KLPK-NH$_2$ (SEQ ID NO:118) | 2.2 | 1.3 |
| AE163 | Ac-LRM k LPK-NH$_2$ (SEQ ID NO:119) | 2.4 | 1.1 |
| AE164 | Ac-LRMK l PK-NH$_2$ (SEQ ID NO:120) | 17.7 | 3.8 |
| AE165 | Ac-LRMKL p K-NH$_2$ (SEQ ID NO:121) | 26.6 | 3.6 |
| AE166 | Ac-LRMKLP k-NH$_2$ (SEQ ID NO:122) | 26.4 | 3.4 |

Table 11: Activities of D-isomer amino acid substitution analogs of AE114. In this assay (as described in Example 1), the concentration of AE101 series peptides was 64 $\mu$M. Lower case letters denote D-amino acid substitutions. The supernatant dilutions taken into the HT-2 cell assays were 1:8 for $E^d$ and 1:4 for $E^k$.

Certain homologs with individual D-isomer amino acid substitutions retain biological activity: AE160, AE164, AE165 and AE166 for $E^d$ and AE164, AE165 and AE166 for $E^k$. In 10 both alleles, the C-terminal three positions tolerate single D-isomer substitutions better than did the C-terminal portion of the AE114 peptide.

TABLE 12

Multiple D-Isomer Substitution Analogs of AE114.

| Peptide | Sequence | $E^d$ | $E^k$ |
|---|---|---|---|
| None | | 1.0 | 1.0 |
| AE114 | Ac-LRMKLPK-NH$_2$ (SEQ ID NO:23) | 103 | 51.5 |
| | | 115 | 19.3 |
| | | 62 | 4.9 |
| | | 5 | 2.1 |
| AE170 | Ac-lrmklpk-NH$_2$ | 1.1 | 2.8 |
| | | 1.2 | 2.4 |
| | | 1.3 | 2.1 |
| | | 1.3 | 1.7 |
| AE171 | Ac-kplkmrl-NH$_2$ | 1.3 | 3.6 |
| | | 1.5 | 2.0 |
| | | 1.4 | 1.4 |
| | | 1.4 | 1.9 |
| AE172 | Ac-LRMKlpk-NH$_2$ (SEQ ID NO:123) | 54 | 46.2 |
| | | 7 | 21.1 |
| | | 2 | 4.2 |
| | | 2 | 2.8 |
| AE173 | Ac-LRMKLpk-NH$_2$ (SEQ ID NO:124) | 123 | 51.3 |
| | | 92 | 25.0 |
| | | 10 | 4.3 |
| | | 2 | 2.1 |

Table 12: Activities of multiple D-isomer substitution analogs of AE114 in a simultaneous assay. In this assay (as described in Example 1), the concentrations of AE101 series peptides were 64 $\mu$M, 16 $\mu$M, 4 $\mu$M and 1 $\mu$M (first through fourth values, respectively) for $E^d$ and $E^k$. Lower case letters denote D-amino acid substitutions. The supernatant dilutions taken into the HT-2 cell assays were 1:2 for $E^d$ and 1:4 for $E^k$.

The all D peptide (AE170) and the "retro-inverso" all D peptide (AE171) were inactive in this assay. In the $E^k$, but not $E^d$ systems, D residues were accepted in the fifth, sixth, and seventh positions of AE114.

Retroinverso peptides (reversed sequence, all D amino acids) sometimes have biological activities of the natural all L amino acid peptides on which they are modeled. The side chain positions are comparable in retro-inverso D and all L peptides, but the backbone is proteolysis-protected. In this case, the retro-inverso all D homolog was inactive, affirming critical steric relationships of both side chain and peptidyl backbone interactions with the receptor. D amino acids were acceptable in the fifth, sixth, and seventh positions, indicating that propteolysis-resistance modifications could be introduced in this region of the peptide without significant loss of biological activity.

Example 4

Certain N-methyl leucine substitutions retain functional activity

A second peptidyl backbone modification intended to a) increase stability and b) test structure-activity relationships along the backbone, was the substitution of N-methyl-leucine for leucine at the first and fifth positions in AE114.

TABLE 13

N-methyl-Leucine Analogs of AE114.

| Peptide | Sequence | $E^d$ | $E^k$ |
|---|---|---|---|
| None | | 1.0 | 1.0 |
| AE114 | Ac-LRMKLPK-NH$_2$ | 48 | 51.5 |
| | (SEQ ID NO:23) | 65 | 19.3 |
| | | 18 | 4.9 |
| | | 2 | 2.1 |
| AE174 | Ac-(mL)RMKLPK-NH$_2$ | 55 | 35.1 |
| | (SEQ ID NO:125) | 40 | 9.8 |
| | | 2 | 3.1 |
| | | 1 | 1.6 |
| AE175 | Ac-LRMK(mL)PK-NH$_2$ | 61 | 59.0 |
| | (SEQ ID NO:126) | 36 | 28.5 |
| | | 6 | 6.5 |
| | | 1 | 2.8 |

Table 13: Activities of N-methyl-leucine substitution analogs of AE114 in a simultaneous assay. In this assay (as described in Example 1), the concentrations of AE101 series peptides were 64 μM, 16 μM, 4 μM and 1 μM (first through fourth values, respectively) for $E^d$ and $E^k$. The supernatant dilutions taken into the HT-2 cell assay were 1:4 for $E^d$ and $E^k$.

N-Methyl leucine is accepted in positions one and five of AE114 with some loss of activity in the $E^d$ system. See below for the effect of N-methyl leucine substitution for methionine in the third position.

TABLE 14

Substitution analogs of AE114.

| Peptide | Sequence | $E^d$ | $E^k$ |
|---|---|---|---|
| None | | 1.0 | 1.0 |
| AE114 | Ac-LRMKLPK-NH$_2$ | 12.4 | 40.3 |
| | (SEQ ID NO:23) | | |
| AE301 | Ac-LRLKYPK-NH$_2$ | 12.5 | 59.9 |
| | (SEQ ID NO:127) | | |
| AE302 | Ac-LR(mL)KLPK-NH$_2$ | 4.5 | 26.1 |
| | (SEQ ID NO:128) | | |
| AE303 | Ac-LR(mL)KYPK-NH$_2$ | 4.0 | 25.3 |
| | (SEQ ID NO:129) | | |
| AE304 | Ac-LR(mL)KyPK-NH$_2$ | 3.9 | 13.4 |
| | (SEQ ID NO:130) | | |
| AE305 | Ac-LR(mL)KYPk-NH$_2$ | 5.2 | 26.8 |
| | (SEQ ID NO:131) | | |
| AE306 | Ac-LR(mL)KyPk-NH$_2$ | 3.2 | 13.7 |
| | (SEQ ID NO:132) | | |

TABLE 14-continued

Substitution analogs of AE114.

| Peptide | Sequence | $E^d$ | $E^k$ |
|---|---|---|---|
| AE307 | Ac-LRLKYPk-NH$_2$ | 13.2 | 56.4 |
| | (SEQ ID NO:133) | | |
| AE308 | Ac-LRLKyPK-NH$_2$ | 12.6 | 45.5 |
| | (SEQ ID NO:134) | | |
| AE309 | Ac-LRLKWPK-NH$_2$ | 12.1 | 48.2 |
| | (SEQ ID NO:135) | | |
| AE235 | Ac-LRMKYPK-NH$_2$ | 12.5 | 56.6 |
| | (SEQ ID NO:92) | | |
| AE206 | Ac-LRLKLPK-NH$_2$ | 12.7 | 53.5 |
| | (SEQ ID NO:70) | | |
| AE166 | Ac-LRMKLPk-NH$_2$ | 14.7 | 40.4 |
| | (SEQ ID NO:121) | | |
| AE164 | Ac-LRMKIPK-NH$_2$ | 12.9 | 43.9 |
| | (SEQ ID NO:120) | | |
| AE174 | Ac-(mL)RMKLPK-NH$_2$ | 15.9 | 34.3 |
| | (SEQ ID NO:125) | | |
| AE175 | Ac-LRMK(mL)PK-NH$_2$ | 15.9 | 58.0 |
| | (SEQ ID NO:126) | | |

Table 14: Activities of substitution analogs of AE114 in a simultaneous assay. The data were generated in a simultaneous assay as described in Example 1. Lower case letters denote D-isomer amino acids, and (mL) denotes N-methyl leucine. The concentration of AE101 series peptides was 64 μM for each allelic system. The supernatant dilutions taken into the HT-2 cell assays were 1:4 for each allelic system.

Substitution of 3-methionine by N-methyl leucine leads to a 50–70% reduction in activity (AE302 versus AE114; AE302 versus AE301). Taken together with the results of substituting N-methyl leucine at the first and third positions in AE174 and AE175, respectively, clearly N-methyl leucine in the first (AE174), third (AE175), and fifth (AE302) positions, respectively, can be exploited to protect against proteolysis.

Furthermore, D amino acids in the fifth position (D-leucine in AE308; D-tyrosine in AE164) and in the seventh position (D-lysine in AE166; D-lysine in AE307) also can protect against proteolysis without a significant loss of activity.

TABLE 15

Multiple substitution analogs of AE114, targeting the $E^d$ allele.

| Peptide | Sequence | $E^d$ | $E^k$ |
|---|---|---|---|
| None | | 1.0 | 1.0 |
| AE114 | Ac-LRMKLPK-NH$_2$ | 228 | 18.2 |
| | (SEQ ID NO:23) | | |
| AE340 | Ac-LR Orn K HArq PK-NH$_2$ | 46.6 | 39.5 |
| | (SEQ ID NO:136) | | |
| AE341 | Ac-LRLK HArg PK-NH$_2$ | 38.9 | 42.4 |
| | (SEQ ID NO:137) | | |
| AE342 | Ac-L Cit MKNPK-NH$_2$ | 2.3 | 5.4 |
| | (SEQ ID NO:138) | | |
| AE343 | Ac-L Cit NKLPK-NH$_2$ | 1.2 | 2.9 |
| | (SEQ ID NO:139) | | |
| AE344 | Ac-ARNKLPK-NH$_2$ | 7.7 | 2.5 |
| | (SEQ ID NO:140) | | |
| AE345 | Ac-ARMKNPK-NH$_2$ | 3.7 | 4.8 |
| | (SEQ ID NO:141) | | |
| AE346 | Ac-ARNKNPK-NH$_2$ | 1.2 | 1.8 |
| | (SEQ ID NO:142) | | |
| AE347 | Ac-ARNKNPF-NH$_2$ | 1.0 | 2.8 |
| | (SEQ ID NO:143) | | |
| AE348 | Ac-LRNKNPF-NH$_2$ | 13.1 | 6.3 |
| | (SEQ ID NO:144) | | |

TABLE 15-continued

Multiple substitution analogs of AE114, targeting the $E^d$ allele.

| Peptide | Sequence | $E^d$ | $E^k$ |
|---|---|---|---|
| AE349 | Ac-LRNKNPK-NH$_2$ (SEQ ID NO:145) | 25.3 | 6.1 |
| AE350 | Ac-LRMKNPF-NH$_2$ (SEQ ID NO:146) | 28.6 | 24.2 |
| AE351 | Ac-A Cit NKNPK-NH$_2$ (SEQ ID NO:147) | 0.8 | 1.6 |
| AE235 | Ac-LRMKYPK-NH$_2$ (SEQ ID NO:92) | 29.4 | 47.7 |
| AE120 | Ac-ARMKLPKSAK-NH$_2$ (SEQ ID NO:107) | 19.4 | 4.8 |
| AE131 | Ac-Y Cit MKLPKSAK-NH$_2$ (SEQ ID NO:47) | 1.6 | 4.1 |
| AE195 | Ac-LR Orn KLPK-NH$_2$ (SEQ ID NO:59) | 34.3 | 19.8 |
| AE202 | Ac-LRNKLPK-NH$_2$ (SEQ ID NO:66) | 34.4 | 5.8 |
| AE206 | Ac-LRLKLPK-NH$_2$ (SEQ ID NO:70) | 25.5 | 35.3 |
| AE227 | Ac-LRMK HArg PK-NH$_2$ (SEQ ID NO:84) | 32.3 | 45.6 |
| AE232 | Ac-LRMKNPK-NH$_2$ (SEQ ID NO:89) | 24.3 | 15.5 |
| AE248 | Ac-LRMKLPF-NH$_2$ (SEQ ID NO:103) | 34.7 | 42.6 |
| AE301 | Ac-LRLKYPK-NH$_2$ (SEQ ID NO:127) | 30.7 | 46.6 |
| AE309 | Ac-LRLKWPK-NH$_2$ (SEQ ID NO:135) | 13.1 | 38.0 |

Table 15: Activities of substitution analogs of AE114 in a simultaneous assay. In this assay (as described in Example 1), the concentration of AE101 series peptides was 16 μM. The supernatant dilutions taken into the HT-2 cell assays were 1:4.

In the above study two approaches were taken to analyze the effect of combinations of individual residue substitutions, each of which as a single substitution favored $E^d$ over $E^k$. First, several combinations of two amino acid substitutions, each of which individually favored $E^d$ over $E^k$, were incorporated into one, new peptide. Alanyl replacements of leucine in the first position led to a loss of activity (AE347 versus AE348; AE202 versus AE344; AE232 versus AE345). Peptides differing only in methionine versus leucine in the third position were always equally active. (AE114 versus AE206; AE235 versus AE301; AE341 versus AE227). In the second approach, three or four individual favored substitutions were combined together in a new peptide. Some of these peptides had high levels of activity.

TABLE 16

Multiple substitution analogs of AE235, targeting the $E^k$ allele.

| Peptide | Sequence | $E^d$ | $E^k$ |
|---|---|---|---|
| None | | 1.0 | 1.0 |
| AE235 | Ac-LRMKYPK-NH$_2$ (SEQ ID NO:92) | 14.3 | 8.4 |
| AE360 | Ac-L HArg MKYPK-NH$_2$ (SEQ ID NO:148) | 5.8 | 2.5 |
| AE361 | Ac-L HArg LKYPK-NH$_2$ (SEQ ID NO:149) | 8.2 | 4.6 |
| AE362 | Ac-LKMKYPK-NH$_2$ (SEQ ID NO:150) | 1.2 | 1.3 |
| AE363 | Ac-LK HArg KYPK-NH$_2$ (SEQ ID NO:151) | 1.6 | 1.7 |

TABLE 16-continued

Multiple substitution analogs of AE235, targeting the $E^k$ allele.

| Peptide | Sequence | $E^d$ | $E^k$ |
|---|---|---|---|
| AE364 | Ac-LRMKYP Cit-NH$_2$ (SEQ ID NO:152) | 14.0 | 16.6 |
| AE365 | Ac-LR HArg MYPK-NH$_2$ (SEQ ID NO:153) | 6.1 | 20.1 |
| AE366 | Ac-LR HArg KYP Cit-NH$_2$ (SEQ ID NO:154) | 7.3 | 49.4 |
| AE367 | Ac-LRMMYP Cit-NH$_2$ (SEQ ID NO:155) | 1.0 | 6.6 |
| AE368 | Ac-LRLKYPN-NH$_2$ (SEQ ID NO:156) | 9.4 | 11.2 |
| AE301 | Ac-LRLKYPK-NH$_2$ (SEQ ID NO:127) | 20.1 | 15.5 |
| AE370 | Ac-LRMKYPN-NH$_2$ (SEQ ID NO:157) | 8.7 | 7.5 |
| AE371 | Ac-FK HArg MYP Cit-NH$_2$ (SEQ ID NO:158) | 1.6 | 1.5 |
| AE114 | Ac-LRMKLPK-NH$_2$ (SEQ ID NO:23) | 15.7 | 1.2 |
| AE132 | Ac-Y HArg MKLPKSAK-NH$_2$ (SEQ ID NO:48) | 3.9 | 2.2 |
| AE134 | Ac-YKMKLPKSAK-NH$_2$ (SEQ ID NO:50) | 1.2 | 1.3 |
| AE206 | Ac-LRLKLPK-NH$_2$ (SEQ ID NO:70) | 15.5 | 1.3 |
| AE197 | Ac-LR HArg KLPK-NH$_2$ (SEQ ID NO:61) | 16.3 | 1.7 |
| AE220 | Ac-LRMMLPK-NH$_2$ (SEQ ID NO:81) | 12.0 | 1.1 |
| AE241 | Ac-LRMKLP Cit-NH$_2$ (SEQ ID NO:96) | 7.1 | 1.0 |
| AE246 | Ac-LRMKLPN-NH$_2$ (SEQ ID NO:101) | 21.8 | 1.0 |
| AE309 | Ac-LRMKWPK-NH$_2$ (SEQ ID NO:135) | 20.0 | 1.8 |

Table 16: Simultaneous assay, substitution analogs of AE114. The data were generated in a simultaneous assay as described in Example 1. The concentration of AE101 series peptides was 4 μM for each allelic system. The supernatant dilutions taken into the HT-2 cell assays were 1:8 for each allelic system.

In the above study two approaches were taken to analyze the effect of combinations of residues, each of which as a single substitution favored $E^d$ over $E^k$. First, several combinations of two amino acid substitutions, each of which individually favored $E^d$ over $E^k$, were incorporated into one, new peptide. While many peptides were comparably active on $E^d$ and $E^k$, some peptides were clearly more active on one allele than on the other. For example, AE114, AE197, AE200 and AE246 all were more than 4 times more active on $E^d$ than on $E^k$. In each of these peptides, the fifth position was filled by leucine and the third position was filled with either leucine or methionine in three peptides with HArg occupying that position in the fourth peptide. Only AE309 had such an $E^d$ preference; it had a tryptophan in the fifth position. In contrast of the two peptides with greater than a 3:1 activity preference for $E^k$ over $E^d$, both had a tyrosyl residue in the fifth position (AE365, AE366) and HArg in the third position.

TABLE 17

Position 5 substitution analogs of AE114.

| Peptide | Sequence | $E^d$ | $E^k$ |
|---|---|---|---|
| None | | 1.0 | 1.0 |
| AE114 | Ac-LRMKLPK-NH$_2$ (SEQ ID NO:23) | 47 | 2.8 |
| AE235 | Ac-LRMKYPK-NH$_2$ (SEQ ID NO:92) | 51 | 26.8 |
| AE322 | Ac-LRMK(X2)PK-NH$_2$ (SEQ ID NO:159) | 37 | 3.0 |
| AE323 | Ac-LRMK(X3)PK-NH$_2$ (SEQ ID NO:159) | 53 | 8.4 |
| AE324 | Ac-LRMK(X4)PK-NH$_2$ (SEQ ID NO:159) | 25 | 3.1 |
| AE325 | Ac-LRMK(X5)PK-NH$_2$ (SEQ ID NO:159) | 49 | 4.7 |
| AE326 | Ac-LRMK(X6)PK-NH$_2$ (SEQ ID NO:159) | 38 | 9.6 |
| AE327 | Ac-LRMK(X8)PK-NH$_2$ (SEQ ID NO:159) | 10 | 2.2 |
| AE328 | Ac-LRMK(X9)PK-NH$_2$ (SEQ ID NO:159) | 4.5 | 2.0 |
| AE329 | Ac-LRMK(X12)PK-NH$_2$ (SEQ ID NO:159) | 35 | 2.8 |
| AE330 | Ac-LRMK(X13)PK-NH$_2$ (SEQ ID NO:159) | 32 | 2.6 |
| AE331 | Ac-LRMK(X14)PK-NH$_2$ (SEQ ID NO:159) | 24 | 12.2 |
| AE332 | Ac-LRMK(X15)PK-NH$_2$ (SEQ ID NO:159) | 29 | 26.4 |

Table 17: Activities of position 5 substitution analogs of AE114 in a simultaneous assay. In this assay (as described in Example 1), the concentration of AE101 series peptides was 4 μM for $E^d$ and 64 μM for $E^k$. The supernatant dilutions taken in the HT-2 cell assays were −1:4 for $E^d$ and 1:4 for $E^k$. The following side chain structures were substituted at position 5: X2=p-chloro-Phe; X3=p-fluoro-Phe; X4=p-nitro-Phe; X5=α-amino-4-phenylbutyrate; X6=β-thienylalanine (Thi); X8=di-bromo-tyrosine; X9=di-iodo-tyrosine; X12=β-1-napthyl-alanine; X13=β-2-napthyl-alanine; X14=1,2,3,4-tetrahydroisoquinoline-3-carboxylic acid (Tic); and X15=1,2,3,4-tetrahydroisoquinoline-7-hydroxy-3-carboxylic acid [Tic(OH)].

The Tic(OH) substitution (AE332) is as potent on $E^k$ as is the 5-tyrosyl reference peptide AE235 The Tic(OH) residue can be superimposed on the tyrosyl structure, with the addition of a methylene bridge between the 2-phenyl carbon and the imido nitrogen in the peptidyl bond of that residue. That bridge mimics proline. Lack of the distal phenolic hydroxyl (AE332 versus AE331) lessens activity. This AE332 Tic(OH) homolog while not significantly more potent than the AE235 tyrosyl homolog is nevertheless much more resistant to proteolysis and can therefor be expected to be considerably more potent in vivo.

TABLE 18

Cyclical analogs of AE-114.

| Peptide | Sequence | $E^d$ | $E^k$ |
|---|---|---|---|
| None | | 1.0 | 1.0 |
| AE114 | Ac-LRMKLPK-NH$_2$ (SEQ ID NO:23) | 12.4 | 40.3 |
| AE381 | cyclic LRMKLPK (SEQ ID NO:23) | 2.1 | 0.56 |
| AE382 | Ac-LRMKLPK (SEQ ID NO:23) | 1.9 | 18.1 |
| AE235 | Ac-LRMKYPK-NH$_2$ (SEQ ID NO:92) | 12.5 | 56.6 |

Table 18: Activities of cyclical analogs of AE114 in a simultaneous assay. In this assay (as described in Example 1), the concentration of the AE101 series peptides was 64 μM. The supernatant dilution taken into the HT-2 cell assays was 1:4 for each allelic system. The AE381 peptide is a "head-to-tail" cyclization from the amino-terminus to the carboxyl-terminus of AE114. The AE382 peptide is a "side-to-tail" cyclization of AE114 from the epsilon-amino group of the 4-lysyl residue to the C-terminal carboxyl group, retaining the amino-terminal acetyl group.

The "head to tail" cyclical peptide AE381 is weak in simultaneous assays on $E^d$ and $E^k$. The "side to tail" cyclical peptide AE382 is moderately active on Ek and relatively inactive on $E^d$. These results contrast to the potent immunosuppressive activities of these peptides in the antigenic peptide prepulse assay (Example 5, Table 18) and the processed antigen assay (Example 6, Table 34). Example 5 : Effect of AE109 and AE114 substitutions on the "peptide prepulse assay"

TABLE 19

C-terminal Truncation Analogs of AE101.

| Peptide | Sequence | $E^d$ | $E^k$ |
|---|---|---|---|
| None | | 1.00 | 1.00 |
| AE109 | Ac-YRMKLPKSAK-NH$_2$ (SEQ ID NO:16) | 0.11 | 0.07 |
| AE167 | Ac-LRMKLPKPPP-NH$_2$ (SEQ ID NO:18) | 0.23 | 0.01 |
| AE168 | Ac-LRMKLPKPPK-NH$_2$ (SEQ ID NO:19) | 0.10 | 0.01 |
| AE113 | Ac-YRMKLPK-NH$_2$ (SEQ ID NO:22) | 0.10 | 0.04 |
| AE115 | Ac-YRMKLP-NH$_2$ (SEQ ID NO:24) | 0.49 | 0.07 |
| AE116 | Ac-YRMKL-NH$_2$ (SEQ ID NO:25) | 0.80 | 0.10 |
| AE117 | Ac-YRMK-NH$_2$ (SEQ ID NO:26) | 0.65 | 0.09 |
| AE118 | Ac-YRM-NH$_2$ (SEQ ID NO:27) | 0.68 | 0.35 |

Table 19: Activities of C-terminal truncation analogs of AE101 in an antigenic peptide prepulse assay. These data were generated in antigenic peptide prepulse assays as described in Example 1 with the following modifications. Paraformaldehyde-treated APC (fixed APC) expressing MHC class II molecules were incubated with antigenic peptide for 6 h (HEL106-116 for $E^d$ and PGCC81-104 for $E^k$). After this incubation, the prepulsed APC were washed and cultured with T hybridoma cells and AE101 series peptides. The antigenic peptide concentration during the prepulse was 12 μM for $E^d$ and 20 μM for $E^k$. The AE101 series peptide concentrations were 64 μM for $E^d$ and 16 μM for $E^k$. The dilutions of supernatant taken into the HT-2 cell assay were 1:4 for $E^d$ and 1:2 for $E^k$.

The results in the $E^d$ allele differed significantly from results in the $E^k$ allele in both this study of the effects of C-terminal truncations of AE113 in the peptide prepulse assay and in the simultaneous assay (Example 1, Table 1). While, in the $E^d$ system, loss of one C-terminal residue (AE115) decreased activity relative to AE113 by half, peptides as short as four amino acids (AE117) retained full activity in both this peptide prepulse assay and in the simultaneous assay (Example 1, Table 1).

TABLE 20

Substitution Series At Arginine[77] (Position 2) in AE109.

| Peptide | Sequence | $E^d$ | $E^k$ |
| --- | --- | --- | --- |
| None | | 1.00 | 1.00 |
| AE101 | YRMKLPKSAKPVSQMR (SEQ ID NO:3) | 0.25 | 0.89 |
| AE109 | Ac-Y R MKLPKSAK-NH$_2$ (SEQ ID NO:16) | 0.28 | 0.28 |
| AE121 | Ac-Y A MKLPKSAK-NH$_2$ (SEQ ID NO:45) | 0.53 | 0.59 |
| AE130 | Ac-Y Orn MKLPKSAK-NH$_2$ (SEQ ID NO:46) | 0.79 | 0.66 |
| AE131 | Ac-Y Cit MKLPKSAK-NH$_2$ (SEQ ID NO:47) | 0.69 | 0.71 |
| AE132 | Ac-Y Harq MKLPKSAK-NH$_2$ (SEQ ID NO:48) | 0.58 | 0.1 |
| AE133 | Ac-Y H MKLPKSAK-NH$_2$ (SEQ ID NO:49) | 0.39 | 0.86 |
| AE134 | Ac-Y K MKLPKSAK-NH$_2$ (SEQ ID NO:50) | 0.60 | 0.43 |
| AE135 | Ac-Y D MKLPKSAK-NH$_2$ (SEQ ID NO:51) | 0.70 | 0.95 |
| AE136 | Ac-Y E MKLPKSAK-NH$_2$ (SEQ ID NO:52) | 0.54 | 0.97 |
| AE137 | Ac-Y N MKLPKSAK-NH$_2$ (SEQ ID NO:53) | 0.57 | 0.72 |
| AE138 | Ac-Y Q MKLPKSAK-NH$_2$ (SEQ ID NO:54) | 0.73 | 0.85 |
| AE139 | Ac-Y F MKLPKSAK-NH$_2$ (SEQ ID NO:55) | 0.67 | 0.38 |
| AE140 | Ac-Y Y MKLPKSAK-NH$_2$ (SEQ ID NO:56) | 0.78 | 0.79 |
| AE141 | Ac-Y M MKLPKSAK-NH$_2$ (SEQ ID NO:57) | 0.41 | 0.52 |
| AE142 | Ac-Y L MKLPKSAK-NH$_2$ (SEQ ID NO:58) | 0.86 | 0.46 |

Table 20: Activities of substitution series at Arginine[77] in AE109 in an antigenic peptide prepulse assay. These data were generated in antigenic peptide prepulse assays carried out as described in Example 1 with the following modifications. The antigenic peptide concentrations during the prepulse was 3 μM for $E^d$ and 20 μM for $E^k$. The AE peptide concentrations were 64 μM for $E^d$ and 16 μM for $E^k$. The supernatant dilutions taken into the HT-2 cell assay were 1:2 for $E^d$ and 1:2 for $E^k$.

The R[77] (position 2) substituted peptides with the greatest activities in the simultaneous assay (Example 1, Table 4) had the greatest activity in the peptide prepulse assay reported here. This mirror imaging of activities in these two assays supports a conclusion of validity about the structure/activity relationships demonstrated in these experiments testing the effects of amino acid replacements at each residue position.

TABLE 21

| Substitution series at Proline[81] (Position 5) in AE109 | | | |
|---|---|---|---|
| Peptide | Sequence | $E^d$ | $E^k$ |
| None | | 1.00 | 1.00 |
| AE109 | Ac—YRMKL P KSAK—$NH_2$ (SEQ ID NO:16) | 0.10 | 0.07 |
| AE143 | Ac—YRMKL hydrP KSAK—$NH_2$ (SEQ ID NO:94) | 0.18 | 0.10 |

Table 21: Activities of hydroxyproline substitution at Proline[81] in an antigenic peptide prepulse assay. In these assays (as described in Example 1), the concentrations of antigenic peptide in the antigen prepulse were 24 $\mu$M for $E^d$ and 20 $\mu$M for $E^k$. The concentrations of AE peptides were 64 $\mu$M for $E^d$ and 16 $\mu$M for $E^k$. The supernatant dilutions taken into the HT-2 cell assay were 1:8 for $E^d$ and 1:2 for $E^k$.

Hydroxyproline at position 5 in AE109 was as potent as proline in the simultaneous assay (Example 1, Table 8) and in the peptide prepulse assay shown here. This result is generally interpreted to mean that there is not a crucial structural interaction between the aliphatic ring of proline and the protein receptor, but instead that the role of the proline is primarily to stabilize local configuration. Since the Tic(OH) structure (an analog of proline) is active, the adjacent placement of proline like Tic(OH) (in the fifth position) to proline in the sixth position creates a type II polyprolyl helix configuration through that region.

TABLE 22

| D amino acid scan analogs of AE114 | | | |
|---|---|---|---|
| Peptide | Sequence | $E^d$ | $E^k$ |
| None | | 1.00 | 1.00 |
| AE114 | Ac—LRMKLPK—$NH_2$ (SEQ ID NO:23) | 0.02 | 0.15 |
| AE160 | Ac—l RMKLPK—$NH_2$ (SEQ ID NO:116) | 0.40 | 0.47 |
| AE161 | Ac—L r MKLPK—$NH_2$ (SEQ ID NO:117) | 0.30 | 0.85 |
| AE162 | Ac—LR m KLPK—$NH_2$ (SEQ ID NO:118) | 0.28 | 0.61 |
| AE163 | Ac—LRM k LPK—$NH_2$ (SEQ ID NO:119) | 0.39 | 0.99 |
| AE164 | Ac—LRMK l PK—$NH_2$ (SEQ ID NO:120) | 0.37 | 0.21 |
| AE165 | Ac—LRMKL p K—$NH_2$ (SEQ ID NO:121) | 0.25 | 0.22 |
| AE166 | Ac—LRMKLP k—$NH_2$ (SEQ ID NO:122) | 0.11 | 0.15 |

Table 22: Activities of D-amino acid substitutions in AE114 in an antigenic peptide prepulse assay. In this assay (as described in Example 1), the concentrations of antigenic peptides in the prepulse were 6 $\mu$M for $E^d$ and 20 $\mu$M for $E^k$. The concentrations of AE101 series peptides were 64 $\mu$M for $E^d$ and 16 $\mu$M for $E^k$. The supernatant dilutions taken into the HT-2 cell assay were 1:8 for $E^d$ and 1:2 for $E^k$.

The activities of AE114 homologs with individual D-amino acid substitutions at each residue position had broadly comparable activities in the simultaneous assay (Example 3, Table 11) and in the peptide prepulse assay reported here. In particular, D-amino acid replacements in residue positions 2 through 5 significantly decreased activity.

TABLE 23

| N-methyl-Leucine Analogs of AE114 | | | |
|---|---|---|---|
| Peptide | Sequence | $E^d$ | $E^k$ |
| None | | 1 | 1 |
| AE114 | Ac—LRMKLPK—$NH_2$ (SEQ ID NO:23) | 0.41 | 0.78 |
| AE174 | Ac—(mL)RMKLPK—$NH_2$ (SEQ ID NO:125) | 0.6 | 0.81 |
| AE175 | Ac—LRMK(mL)PK—$NH_2$ (SEQ ID NO:126) | 0.7 | 0.87 |

Table 23: Activities of N-methyl-leucine analogs of AE114 in an antigenic peptide prepulse assay. In this assay (as described in Example 1), the concentrations of antigenic peptides during the prepulse were 64 $\mu$M for $E^d$ and 64 $\mu$M for $E^k$. The concentrations of AE101 series peptides used were 1:4 $\mu$M for $E^d$ and 1:8 $\mu$M for $E^k$. The supernatant dilutions taken into the HT-2 cell assay were 1:8 for $E^d$ and 1:2 for $E^k$.

As in the simultaneous assay with these N-methyl-leucine substitutions (Example 4, Table [13]), N-methyl-leucine substitutions had a small degree of activity loss relative to the control peptide AE114. Such substitutions might be expected in vivo to lead to increased potency due to proteolysis protection of these substrates.

TABLE 24

Substitution analogs of AE-114

| Peptide | Sequence | $E^d$ | $E^k$ |
|---|---|---|---|
| None | | 1.00 | 1.00 |
| AE114 | Ac—LRMKLPK—NH$_2$ (SEQ ID NO:23) | 0.41 | 0.78 |
| AE301 | Ac—LRLKYPK—NH$_2$ (SEQ ID NO:127) | 0.48 | 0.80 |
| AE302 | Ac—LR(mL)KLPK—NH$_2$ (SEQ ID NO:128) | 0.82 | 0.85 |
| AE303 | Ac—LR(mL)KYPK—NH$_2$ (SEQ ID NO:129) | 0.78 | 1.00 |
| AE304 | Ac—LR(mL)KyPK—NH$_2$ (SEQ ID NO:130) | 0.78 | 0.76 |
| AE305 | Ac—LR(mL)KYPk—NH$_2$ (SEQ ID NO:131) | 0.72 | 0.91 |
| AE306 | Ac—LR(mL)KyPk—NH$_2$ (SEQ ID NO:132) | 0.68 | 1.00 |
| AE307 | Ac—LRLKYPk—NH$_2$ (SEQ ID NO:133) | 0.59 | 1.10 |
| AE308 | Ac—LRLKyPK—NH$_2$ (SEQ ID NO:134) | 0.93 | 0.63 |
| AE309 | Ac—LRLKWPK—NH$_2$ (SEQ ID NO:135) | 0.44 | 0.81 |
| AE235 | Ac—LRMKYPK—NH$_2$ (SEQ ID NO:92) | 0.30 | 0.80 |
| AE206 | Ac—LRLKLPK—NH$_2$ (SEQ ID NO:70) | 0.52 | 1.00 |
| AE166 | Ac—LRMKLPk—NH$_2$ (SEQ ID NO:122) | 0.65 | 0.83 |
| AE164 | Ac—LRMKlPK—NH$_2$ (SEQ ID NO:120) | 0.59 | 0.67 |
| AE174 | Ac—(mL)RMKLPK—NH$_2$ (SEQ ID NO:125) | 0.60 | 0.81 |
| AE175 | Ac—LRMK(mL)PK—NH$_2$ (SEQ ID NO:126) | 0.70 | 0.87 |

Table 24: Activities of substitution analogs of AE114 in an antigenic peptide prepulse assay. In this assay (as described in Example 1), the concentrations of antigenic peptides during the prepulse were 24 µM for $E^d$ and 0.625 µM for $E^k$. The concentrations of AE101 series peptides used were 64 µM for $E^d$ and 64 µM for $E^k$. The supernatant dilutions taken into the HT-2 cell assay were 1:4 for $E^d$ and 1:8 for $E^k$.

The results in this assay constitute, relatively, a mirror image of the result in the simultaneous assay (Table 14) Substitutions of Met[3] by N-methyl-leucine led to a loss of activity compared to AE114. Furthermore, D amino acids in the fifth position (D-leucine in AE308; D-tyrosine in AE164) and in the seventh position (D-lysine in AE166; D-lysine in AE307) also can protect against proteolysis without a significant loss of activity.

TABLE 25

Multiple substitution analogs of AE-114, targeting the $E^d$ allele

| Peptide | Sequence | $E^d$ | $E^k$ |
|---|---|---|---|
| None | | 1.00 | 1.00 |
| AE114 | Ac—LRMKLPK—NH$_2$ (SEQ ID NO:23) | 0.31 | 0.79 |
| AE340 | Ac—LR Orn K Harg PK—NH$_2$ (SEQ ID NO:136) | 0.10 | 0.83 |

TABLE 25-continued

Multiple substitution analogs of AE-114, targeting the $E^d$ allele

| Peptide | Sequence | $E^d$ | $E^k$ |
|---|---|---|---|
| AE341 | Ac—LRLK Harg PK—NH$_2$ (SEQ ID NO:137) | 0.12 | 1.10 |
| AE342 | Ac—L Cit MKNPK—NH$_2$ (SEQ ID NO:138) | 0.67 | 1.10 |
| AE343 | Ac—L Cit NKLPK—NH$_2$ (SEQ ID NO:139) | 0.55 | 0.90 |
| AE344 | Ac—ARNKLPK—NH$_2$ (SEQ ID NO:140) | 0.46 | 0.76 |
| AE345 | Ac—ARMKNPK—NH$_2$ (SEQ ID NO:141) | 0.61 | 0.86 |
| AE346 | Ac—ARNKNPK—NH$_2$ (SEQ ID NO:142) | 0.65 | 0.77 |
| AE347 | Ac—ARNKNPF—NH$_2$ (SEQ ID NO:143) | 0.64 | 1.10 |
| AE348 | Ac—LRNKNPF—NH$_2$ (SEQ ID NO:144) | 0.39 | 0.72 |
| AE349 | Ac—LRNKNPK—NH$_2$ (SEQ ID NO:145) | 0.69 | 0.81 |
| AE350 | Ac—LRMKNPF—NH$_2$ (SEQ ID NO:146) | 0.82 | 0.86 |
| AE351 | Ac—A Cit NKNPK—NH$_2$ (SEQ ID NO:147) | 0.42 | 0.90 |
| AE235 | Ac—LRMKYPK—NH$_2$ (SEQ ID NO:92) | 0.25 | 0.76 |
| AE120 | Ac—ARMKLPKSAK—NH$_2$ | 0.63 | 0.62 |
| AE131 | Ac—Y Cit MKLPKSAK—NH$_2$ (SEQ ID NO:47) | 0.61 | 0.98 |
| AE195 | Ac—LR Orn KLPK—NH$_2$ (SEQ ID NO:59) | 0.41 | 0.74 |
| AE202 | Ac—LRNKLPK—NH$_2$ (SEQ ID NO:66) | 0.30 | 0.84 |
| AE206 | Ac—LRLKLPK—NH$_2$ (SEQ ID NO:70) | 0.18 | 0.68 |
| AE227 | Ac—LRMK Harg PK—NH$_2$ (SEQ ID NO:84) | 0.28 | 0.87 |
| AE232 | Ac—LRMKNPK—NH$_2$ (SEQ ID NO:89) | 0.44 | 0.92 |
| AE248 | Ac—LRMKLPF—NH$_2$ (SEQ ID NO:103) | 0.63 | 0.98 |
| AE301 | Ac—LRLKYPK—NH$_2$ (SEQ ID NO:127) | 0.66 | 0.86 |
| AE309 | Ac—LRLKWPK—NH$_2$ (SEQ ID NO:135) | 0.48 | 0.93 |

Table 25: Activities of multiple substitution analogs of AE114, targeting the $E^d$ allele, in the antigenic peptide prepulse assay. In this assay (as described in Example 1), the concentrations of antigenic peptides during the prepulse were 24 µM for $E^d$ and 2.5 µM for $E^k$. The concentrations of AE101 series peptides used were 64 µM for $E^d$ and 64 µM for $E^k$. The supernatant dilutions taken into the HT-2 cell assay were 1:4 for $E^d$ and 1:10 for $E^k$.

The results in these assays parallel the results in the simultaneous assay (Example 4, Table 15).

TABLE 26

Multiple substitution analogs of AE235, targeting the $E^k$ allele

| Peptide | Sequence | $E^d$ | $E^k$ |
|---|---|---|---|
| None | | 1.0 | 1.0 |
| AE235 | Ac—LRMKYPK—NH$_2$ (SEQ ID NO:92) | 0.23 | 0.60 |
| AE360 | Ac—L Harg MKYPK—NH$_2$ (SEQ ID NO:148) | 0.91 | 0.94 |
| AE361 | Ac—L Harg LKYPK—NH$_2$ (SEQ ID NO:149) | 0.83 | 1.00 |

TABLE 26-continued

Multiple substitution analogs of AE235, targeting the $E^k$ allele

| Peptide | Sequence | $E^d$ | $E^k$ |
|---|---|---|---|
| AE362 | Ac—LKMKYPK—NH$_2$ (SEQ ID NO:150) | 0.76 | 0.91 |
| AE363 | Ac—LK Harg KYPK—NH$_2$ (SEQ ID NO:151) | 0.60 | 0.97 |
| AE364 | Ac—LRMKYP Cit—NH$_2$ (SEQ ID NO:152) | 0.34 | 0.93 |
| AE365 | Ac—LR Harg MYPK—NH$_2$ (SEQ ID NO:153) | 0.70 | 0.42 |
| AE366 | Ac—LR Harg KYP Cit—NH$_2$ (SEQ ID NO:154) | 0.44 | 0.94 |
| AE367 | Ac—LRMMYP Cit—NH$_2$ (SEQ ID NO:155) | 1.10 | 0.99 |
| AE368 | Ac—LRLKYPN—NH$_2$ (SEQ ID NO:156) | 0.55 | 0.92 |
| AE301 | Ac—LRLKYPK—NH$_2$ (SEQ ID NO:127) | 0.34 | 0.99 |
| AE370 | Ac—LRMKYPN—NH2 (SEQ ID NO:157) | 0.74 | 0.58 |
| AE371 | Ac—FK Harg MYP Cit—NH$_2$ (SEQ ID NO:158) | 0.90 | 0.99 |
| AE114 | Ac—LRMKLPK—NH$_2$ (SEQ ID NO:23) | 0.28 | 0.98 |
| AE132 | Ac—Y Harg MKLPKSAK—NH$_2$ (SEQ ID NO:48) | 0.82 | 0.89 |
| AE134 | Ac—YKMKLPKSAK—NH$_2$ (SEQ ID NO:50) | 0.83 | 0.98 |
| AE206 | Ac—LRLKLPK—NH$_2$ (SEQ ID NO:70) | 0.38 | 0.96 |
| AE197 | Ac—LR Harg KLPK—NH$_2$ (SEQ ID NO:61) | 0.32 | 0.96 |
| AE220 | Ac—LRMMLPK—NH$_2$ (SEQ ID NO:81) | 0.73 | 0.92 |
| AE241 | Ac—LRMKLP Cit—NH$_2$ (SEQ ID NO:96) | 0.70 | 0.99 |
| AE246 | Ac—LRMKLPN—NH$_2$ (SEQ ID NO:101) | 0.69 | 0.98 |
| AE309 | Ac—LRMKWPK—NH$_2$ (SEQ ID NO:135) | 0.25 | 0.98 |

Table 26: Activities of multiple substitution analogs of AE235, targeting the $E^k$ allele, in an antigenic peptide prepulse assay. In this assay (as described in Example 1), the concentrations of antigenic peptides during the prepulse were 24 μM for $E^d$ and 1.25 μM for $E^k$. The concentrations of AE101 series peptides used were 64 μM for $E^d$ and 64 μM for $E^k$. The supernatant dilutions taken into the HT-2 cell assay were 1:2 for $E^d$ and 1:8 for $E^k$.

Activities of individual AE101 series peptides in this assay paralleled their level of activity in the simultaneous assay (Example 4, Table 15).

TABLE 27

Position 5 substitution analogs of AE114

| Peptide | Sequence | $E^d$ | $E^k$ |
|---|---|---|---|
| None | | 1.0 | 1.0 |
| AE114 | Ac—LRMKLPK—NH$_2$ (SEQ ID NO:23) | 0.32 | 0.69 |
| AE235 | Ac—LRMKYPK—NH$_2$ (SEQ ID NO:92) | 0.40 | 0.83 |
| AE322 | Ac—LRMK(X2)PK—NH$_2$ (SEQ ID NO:159) | 0.42 | 0.64 |
| AE323 | Ac—LRMK(X3)PK—NH$_2$ (SEQ ID NO:159) | 0.19 | 0.50 |
| AE324 | Ac—LRMK(X4)PK—NH$_2$ (SEQ ID NO:159) | 0.44 | 0.68 |
| AE325 | Ac—LRMK(X5)PK—NH$_2$ (SEQ ID NO:159) | 0.18 | 0.58 |

TABLE 27-continued

Position 5 substitution analogs of AE114

| Peptide | Sequence | $E^d$ | $E^k$ |
|---|---|---|---|
| AE326 | Ac—LRMK(X6)PK—NH$_2$ (SEQ ID NO:159) | 0.40 | 0.52 |
| AE327 | Ac—LRMK(X8)PK—NH$_2$ (SEQ ID NO:159) | 0.74 | 0.99 |
| AE328 | Ac—LRMK(X9)PK—NH$_2$ (SEQ ID NO:159) | 0.71 | 0.74 |
| AE329 | Ac—LRMK(X12)PK—NH$_2$ (SEQ ID NO:159) | 0.34 | 0.40 |
| AE330 | Ac—LRMK(X13)PK—NH$_2$ (SEQ ID NO:159) | 0.25 | 0.37 |
| AE331 | Ac—LRMK(X14)PK—NH$_2$ (SEQ ID NO:159) | 0.40 | 0.84 |
| AE332 | Ac—LRMK(X15)PK—NH$_2$ (SEQ ID NO:159) | 0.33 | 0.61 |

Table 27: Activities of position 5 substitution analogs in an antigenic peptide prepulse assay. In this assay (as described in Example 1), the concentrations of antigenic peptides during the prepulse were 24 μM for $E^d$ and 1.25 μM for $E^k$. The concentrations of AE101 series peptides used were 64 μM for $E^d$ and 64 μM for $E^k$. The supernatant dilutions taken into the HT-2 cell assay was 1:8 for $E^d$ and 1:8 for $E^k$. The following side chain structures were substituted at position 5: X2=p-chloro-Phe; X3=p-fluoro-Phe; X4=p-nitro-Phe; X5=α-amino-4-phenylbutyrate; X6=β-thienylalanine (Thi); X8=di-bromo-tyrosine; X9=di-iodo-tyrosine; X12=β-1-napthyl-alanine; X13=β-2-napthyl-alanine; X14=1,2,3,4-tetrahydroisoquinoline-3-carboxylic acid (Tic); and X15=1,2,3,4-tetrahydroisoquinoline-7-hydroxy-3-carboxylic acid [Tic(OH)].

Activities of individual AE101 series peptides in this assay paralleled their level of activity in the simultaneous assay (Example 4, Table 17).

TABLE 28

Cyclical analogs of AE-114

| Peptide | Sequence | $E^d$ | $E^k$ |
|---|---|---|---|
| None | | 1.0 | 1.0 |
| AE114 | Ac—LRMKLPK—NH$_2$ (SEQ ID NO:23) | 0.41 | 0.78 |
| AE381 | Ac—<u>L</u>RMKLP<u>K</u>—NH$_2$ (SEQ ID NO:23) | 0.19 | 0.28 |
| AE382 | Ac—LRM<u>K</u>LP<u>K</u>—NH$_2$ (SEQ ID NO:23) | 0.52 | 0.70 |
| AE235 | Ac—LRMKYPK—NH$_2$ (SEQ ID NO:92) | 0.30 | 0.80 |

Table 28: Activities of multiple substitution analogs of AE235, targeting the $E^k$ allele, in an antigenic peptide prepulse assay. In this assay (as described in Example 1), the concentrations of antigenic peptides during the prepulse were 24 μM for $E^d$ and 1.25 μM for $E^k$. The concentrations of AE101 series peptides used were 64 μM for $E^d$ and $E^k$. The supernatant dilutions taken into the HT-2 cell assay were 1:4 for $E^d$ and $E^k$.

In sharp contrast to the pattern with all linear AE101 series peptides, wherein the activity in the antigenic prepulse assay was the mirror image of activity in the simultaneous assay, the "head-to-tail" cyclical peptide AE381 was significantly more active in the antigenic peptide prepulse assay than in the simultaneous assay. This finding is consistent with the hypothesis that this cyclic peptide binds very tightly to the allosteric effector site in a fashion which did not permit entry of a second antigenic peptide in to the antigenic peptide binding site of the MHC class II molecules.

Example 6

Effects on the "processed antigen" assay:

The "processed antigen assay" was carried out under essentially the same conditions as the "peptide prepulse" assay, with the following modifications. Untreated APC were incubated at 1×10⁶/mL in 24-well plates (1 mL/well) with native protein antigen for 8 h. Following incubation, the pulsed APC were washed, treated with mitomycin C, and were washed again. The assay conditions were then as described for "peptide prepulse" above. The baseline T cell response was measured by culturing T hybridoma cells with the native antigen-prepulsed APC in the absence of AE101 peptides.

TABLE 29

Leucine$^{80}$ analogs of AE114

| Peptide | Sequence | 20 μM HEL E$^d$ | 10 μM HEL E$^d$ | 5 μM HEL E$^d$ |
|---|---|---|---|---|
| None | | 1.0, 1.0 | 1.0, 1.0 | 1.0, 1.0 |
| AE114 | Ac—LRMK L PK—NH₂ (SEQ ID NO:23) | 0.53, 0.44 | 0.29, 0.28 | 0.23, 0.37 |
| AE225 | Ac—LRMK Orn PK—NH₂ (SEQ ID NO:82) | 0.59, 0.48 | 0.32, 0.30 | 0.26, 0.38 |
| AE226 | Ac—LRMK Cit PK—NH₂ (SEQ ID NO:83) | 0.95, 0.87 | 0.68, 0.58 | 0.60, 0.34 |
| AE227 | Ac—LRMK HargPK—NH₂ (SEQ ID NO:84) | 0.45, 0.36 | 0.18, 0.19 | 0.18, 0.33 |
| AE228 | Ac—LRMK H PK—NH₂ (SEQ ID NO:85) | 0.71, 0.61 | 0.41, 0.41 | 0.35, 0.45 |
| AE229 | Ac—LRMK K PK—NH₂ (SEQ ID NO:86) | 0.71, 0.62 | 0.55, 0.49 | 0.38, 0.58 |
| AE230 | Ac—LRMK D PK—NH₂ (SEQ ID NO:87) | 1.1, 0.98 | 0.93, 0.77 | 0.81, 0.62 |
| AE231 | Ac—LRMK E PK—NH₂ (SEQ ID NO:88) | 1.0, 1.1 | 0.94, 0.83 | 0.96, 0.85 |
| AE232 | Ac—LRMK N PK—NH₂ (SEQ ID NO:89) | 0.97, 0.83 | 0.68, 0.61 | 0.50, 0.50 |
| AE233 | Ac—LRMK Q PK—NH₂ (SEQ ID NO:90) | 0.74, 0.68 | 0.53, 0.47 | 0.48, 0.36 |
| AE234 | Ac—LRMK F PK—NH₂ (SEQ ID NO:91) | 0.98, 0.88 | 0.65, 0.60 | 0.51, 0.62 |
| AE235 | Ac—LRMK Y PK—NH₂ (SEQ ID NO:92) | 0.71, 0.56 | 0.42, 0.39 | 0.33, 0.38 |
| AE236 | Ac—LRMK M PK—NH₂ (SEQ ID NO:93) | 0.76, 0.72 | 0.56, 0.53 | 0.41, 0.58 |

Table 29: Activities of substitution series at Leucine$^{80}$ in AE114 in a processed antigen assay. These data presented were generated as described in the legend of Table 14, with the following modifications. The results in this assay constitute, relatively, a mirror image of the result in the simultaneous assay (Example 1, Table 7) and parallel those of the antigenic peptide prepulse assay (Example 5, Table 24). Untreated APC were incubated with native HEL, instead of antigenic peptide, for 8 h. After incubation, the pulsed cells were washed and mitomycin C treated before being cocultured with AE peptides and T cell hybridomas. Wells containing only T cells and native HEL-prepulsed APC were used to determine the Baseline response, or 1, in the absence of AE peptides. The concentration of AE peptide used was 64 μM for these assays. The supernatant dilutions used in the HT-2 cell assay were 1:4 (first value) and 1:8 (second value).

AE114 homologs with various amino acid substitutions in the fifth position which were most potent in the simultaneous assay (Example 1, Table 7) and in a peptide prepulse assay (Example 5, Table 15) were most active in this processed antigen assay.

TABLE 30

Substitution analogs of AE-114

| Peptide | Sequence | E$^d$ |
|---|---|---|
| None | | 1.0 |
| AE114 | Ac—LRMKLPK—NH₂ (SEQ ID NO:23) | 0.22 |
| AE301 | Ac—LRLKYPK—NH₂ (SEQ ID NO:127) | 0.19 |
| AE302 | Ac—LR(mL)KLPK—NH₂ (SEQ ID NO:128) | 0.51 |
| AE303 | Ac—LR(mL)KYPK—NH₂ (SEQ ID NO:129) | 0.82 |
| AE304 | Ac—LR(mL)KyPK—NH₂ (SEQ ID NO:130) | 0.77 |
| AE305 | Ac—LR(mL)KYPk—NH₂ (SEQ ID NO:131) | 0.70 |
| AE306 | Ac—LR(mL)KyPk—NH₂ (SEQ ID NO:132) | 0.68 |
| AE307 | Ac—LRLKYPk—NH₂ (SEQ ID NO:133) | 0.48 |
| AE308 | Ac—LRLKyPK—NH₂ (SEQ ID NO:134) | 0.60 |
| AE309 | Ac—LRLKWPK—NH₂ (SEQ ID NO:135) | 0.29 |
| AE235 | Ac—LRMKYPK—NH₂ (SEQ ID NO:92) | 0.19 |
| AE206 | Ac—LRLKLPK—NH₂ (SEQ ID NO:70) | 0.22 |
| AE166 | Ac—LRMKLPk—NH₂ (SEQ ID NO:122) | 0.36 |
| AE164 | Ac—LRMKlPK—NH₂ (SEQ ID NO:120) | 0.64 |
| AE174 | Ac—(mL)RMKLPK—NH₂ (SEQ ID NO:125) | 0.86 |
| AE175 | Ac—LRMK(mL)PK—NH₂ (SEQ ID NO:126) | 0.70 |

Table 30: Activities of substitution analogs of AE114 in a processed antigen assay. In this assay (as described in the legend of Table 30) the concentration of native HEL used during the prepulse was 10 μM. The concentration of AE peptide used was 64 μM for this assay. The supernatant dilution used in the HT-2 cell assay was 1:8.

The results in this assay constitute, relatively, a mirror image of the result in the simultaneous assay (Example 1, Table 14) and parallel those of the antigenic peptide prepulse assay (Example 5, Table 24). Substitutions of Met$^3$ by N-methyl-leucine led to a loss of activity compared to AE114. Furthermore, D amino acids in the fifth position (D-leucine in AE308; D-tyrosine in AE164) and in the seventh position (D-lysine in AE166; D-lysine in AE307) also can protect against proteolysis without a significant loss of activity.

TABLE 31

Multiple substitution analogs of AE114, targeting the E$^d$ allele

| Peptide | Sequence | E$^d$ |
|---|---|---|
| None peptide | | 1.00 |
| AE114 | Ac—LRMKLPK—NH₂ (SEQ ID NO:23) | 0.49 |
| AE340 | Ac—LR Orn K Harg PK—NH₂ (SEQ ID NO:136) | 0.16 |
| AE341 | Ac—LRLK Harg PK—NH₂ (SEQ ID NO:137) | 0.12 |
| AE342 | Ac—L Cit MKNPK—NH₂ (SEQ ID NO:138) | 0.64 |

TABLE 31-continued

Multiple substitution analogs of AE114, targeting the $E^d$ allele

| Peptide | Sequence | $E^d$ |
|---|---|---|
| AE343 | Ac—L Cit NKLPK—NH$_2$ (SEQ ID NO:139) | 0.69 |
| AE344 | Ac—ARNKLPK—NH$_2$ (SEQ ID NO:140) | 0.76 |
| AE345 | Ac—ARMKNPK—NH$_2$ (SEQ ID NO:141) | 0.81 |
| AE346 | Ac—ARNKNPK—NH$_2$ (SEQ ID NO:142) | 0.78 |
| AE347 | Ac—ARNKNPF—NH$_2$ (SEQ ID NO:143) | 0.80 |
| AE348 | Ac—LRNKNPF—NH$_2$ (SEQ ID NO:144) | 0.81 |
| AE349 | Ac—LRNKNPK—NH$_2$ (SEQ ID NO:145) | 0.64 |
| AE350 | Ac—LRMKNPF—NH$_2$ (SEQ ID NO:146) | 0.56 |
| AE351 | Ac—A Cit NKNPK—NH$_2$ (SEQ ID NO:147) | 0.87 |
| AE235 | Ac—LRMKYPK—NH$_2$ (SEQ ID NO:92) | 0.53 |
| AE120 | Ac—ARMKLPKSAK—NH$_2$ (SEQ ID NO:107) | 0.51 |
| AE131 | Ac—Y Cit MKLPKSAK—NH$_2$ (SEQ ID NO:47) | 0.49 |
| AE195 | Ac—LR Orn KLPK—NH$_2$ (SEQ ID NO:59) | 0.31 |
| AE202 | Ac—LRNKLPK—NH$_2$ (SEQ ID NO:66) | 0.76 |
| AE206 | Ac—LRLKLPK—NH$_2$ (SEQ ID NO:70) | 0.41 |
| AE227 | Ac—LRMK Harg PK—NH$_2$ (SEQ ID NO:84) | 0.35 |
| AE232 | Ac—LRMKNPK—NH$_2$ (SEQ ID NO:89) | 0.46 |
| AE248 | Ac—LRMKLPF—NH$_2$ (SEQ ID NO:103) | 0.30 |
| AE301 | Ac—LRLKYPK—NH$_2$ (SEQ ID NO:127) | 0.46 |
| AE309 | Ac—LRLKWPK—NH$_2$ (SEQ ID NO:135) | 0.44 |

Table 31: Activities of multiple substitution analogs of AE114, targeting the $E^d$ allele, in a processed antigen assay. In this assay (as described in the legend of Table 30), the concentration of native HEL used during the prepulse was 10 $\mu$M. The concentration of AE peptide used was 64 $\mu$M for this assay. The supernatant dilution used in the HT-2 cell assay was 1:4.

The results in this assay constitute, relatively, a mirror image of the result in the simultaneous assay (Example 1, Table 15) and parallel those of the antigenic peptide prepulse assay (Example 5, Table 25).

TABLE 32

Multiple substitution analogs of AE235, targeting the $E^k$ allele.

| Peptide | Sequence | $E^d$ |
|---|---|---|
| None | | 1.0 |
| AE235 | Ac-LRMKYPK-NH$_2$ (SEQ ID NO:92) | 0.46 |
| AE360 | Ac-L Harg MKYPK-NH$_2$ (SEQ ID NO:148) | 0.64 |
| AE361 | Ac-L Harg LKYPK-NH$_2$ (SEQ ID NO:149) | 0.51 |
| AE362 | Ac-LKMKYPK-NH$_2$ (SEQ ID NO:150) | 0.58 |

TABLE 32-continued

Multiple substitution analogs of AE235, targeting the $E^k$ allele.

| Peptide | Sequence | $E^d$ |
|---|---|---|
| AE363 | Ac-LK Harg KYPK-NH$_2$ (SEQ ID NO:151) | 0.75 |
| AE364 | Ac-LRMKYP Cit-NH$_2$ (SEQ ID NO:152) | 0.56 |
| AE365 | Ac-LR Harg MYPK-NH$_2$ (SEQ ID NO:153) | 0.65 |
| AE366 | Ac-LR Harg KYP Cit-NH$_2$ (SEQ ID NO:154) | 0.53 |
| AE367 | Ac-LRMMYP Cit-NH$_2$ (SEQ ID NO:155) | 0.69 |
| AE368 | Ac-LRLKYPN-NH$_2$ (SEQ ID NO:156) | 0.55 |
| AE301 | Ac-LRLKYPK-NH$_2$ (SEQ ID NO:127) | 0.54 |
| AE370 | Ac-LRMKYPN-NH$_2$ (SEQ ID NO:157) | 0.55 |
| AE371 | Ac-FK Harg MYP Cit-NH$_2$ (SEQ ID NO:158) | 0.61 |
| AE114 | Ac-LRMKLPK-NH$_2$ (SEQ ID NO:23) | 0.40 |
| AE132 | Ac-Y Harg MKLPKSAK-NH$_2$ (SEQ ID NO:48) | 0.48 |
| AE134 | Ac-YKMKLPKSAK-NH$_2$ (SEQ ID NO:50) | 0.50 |
| AE206 | Ac-LRLKLPK-NH$_2$ (SEQ ID NO:70) | 0.46 |
| AE197 | Ac-LR HargKLPK-NH$_2$ (SEQ ID NO:61) | 0.45 |
| AE220 | Ac-LRMMLPK-NH$_2$ (SEQ ID NO:81) | 0.63 |
| AE241 | Ac-LRMKLP Cit-NH$_2$ (SEQ ID NO:96) | 0.63 |
| AE246 | Ac-LRMKLPN-NH$_2$ (SEQ ID NO:101) | 0.72 |
| AE309 | Ac-LRMKWPK-NH$_2$ (SEQ ID NO:135) | 0.55 |

Table 32: Activities of multiple substitution analogs of AE114, targeting the $E^k$ allele, in a processed antigen assay. In this assay (as described in the legend of Table 30), the concentration of native HEL used during the prepulse was 20 $\mu$M. The concentration of AE peptide used was 64 $\mu$M for this assay. The supernatant dilution used in the HT-2 cell assay was 1:4.

The results in this assay constitute, relatively, a mirror image of the result in the simultaneous assay (Example 1, Table 16) and parallel those of the antigenic peptide prepulse assay (Example 5, Table 26).

TABLE 33

Position 5 substitution analogs of AE114.

| Peptide | Sequence | $E^d$ |
|---|---|---|
| None | | 1.0 |
| AE114 | Ac-LRMKLPK-NH$_2$ (SEQ ID NO:23) | 0.37 |
| AE235 | Ac-LRMKYPK-NH$_2$ (SEQ ID NO:92) | 0.45 |
| AE322 | Ac-LRMK(X1)PK-NH$_2$ (SEQ ID NO:159) | 0.41 |
| AE323 | Ac-LRMK(X3)PK-NH$_2$ (SEQ ID NO:159) | 0.25 |
| AE324 | Ac-LRMK(X4)PK-NH$_2$ (SEQ ID NO:159) | 0.42 |
| AE325 | Ac-LRMK(X5)PK-NH$_2$ (SEQ ID NO:159) | 0.33 |
| AE326 | Ac-LRMK(X6)PK-NH$_2$ (SEQ ID NO:159) | 0.38 |
| AE327 | Ac-LRMK(X8)PK-NH$_2$ (SEQ ID NO:159) | 0.60 |

TABLE 33-continued

Position 5 substitution analogs of AE114.

| Peptide | Sequence | $E^d$ |
|---|---|---|
| AE328 | Ac-LRMK(X9).PK-NH$_2$ (SEQ ID NO:159) | 0.66 |
| AE329 | Ac-LRMK(X12)PK-NH$_2$ (SEQ ID NO:159) | 0.32 |
| AE330 | Ac-LRMK(X13)PK-NH$_2$ (SEQ. ID NO:159) | 0.27 |
| AE331 | Ac-LRMK(X14)PK-NH$_2$ (SEQ ID NO:159) | 0.50 |
| AE332 | Ac-LRMK(X15)PK-NH$_2$ (SEQ ID NO:159) | 0.48 |

Table 33: Activities of position 5 substitution analogs of AE114 in a processed antigen assay. In this assay (as described in the legend of Table 30) the concentration of native HEL used during the prepulse was 10 μM. The concentration of AE peptide used was 64 μM for this assay. The supernatant dilution used in the HT-2 cell assay was 1:8. The following side chain structures were substituted at position 5: X2=p-chloro-Phe; X3=p-fluoro-Phe; X4=p-nitro-Phe; X5=α-amino-4-phenylbutyrate; X6=β-thienylalanine (Thi); X8=di-bromo-tyrosine; X9=di-iodo-tyrosine; X12=β-1-napthyl-alanine; X13=β-2-napthyl-alanine; X14=1,2,3,4-tetrahydroisoquinoline-3-carboxylic acid (Tic); and X15=1,2,3,4-tetrahydroisoquinoline-7-hydroxy-3-carboxylic acid [Tic(OH)].

The results in this assay constitute, relatively, a mirror image of the result in the simultaneous assay (Example 1, Table 17 and parallel those of the antigenic peptide prepulse assay (Example 5, Table 27).

TABLE 34

Cyclical analogs of AE-114.

| Peptide | Sequence | $E^d$ |
|---|---|---|
| None | | 1.0 |
| AE114 | Ac-LRMKLPK-NH$_2$ (SEQ ID NO:23) | 0.22 |
| AE381 | Ac-LRMKLPK-NH$_2$ (SEQ ID NO:23) | 0.18 |
| AE382 | Ac-LRMKLPK-NH$_2$ (SEQ ID NO:23) | 0.61 |
| AE235 | Ac-LRMKYPK-NH$_2$ (SEQ ID NO:92) | 0.19 |

Table 34: Activities of cyclical analogs of AE114 in a processed antigen assay. In this assay (as described in the legend of Table 30) the concentration of AE peptide used was 64 μM for this assay. The supernatant dilution used in the HT-2 cell assay was 1:8. The AE381 peptide is a head-to-tail cyclization: the amino terminal amino group is coupled through an amide linkage to the carboxyl terminal group. The AE 382 peptide is a side-to-tail cyclization: the epsilon amino group of Lys$^4$ is coupled through an amide linkage to the carboxyl terminal group. The concentration of native HEL used during the prepulse was 10 μM.

The results in this assay constitute, relatively, a mirror image of the result in the simultaneous assay (Example 1, Table 18) and parallel those of the antigenic peptide prepulse assay (Example 5, Table 28).

TABLE 35

Activities of multiple substitution analogs of AE235 in an AE101 series peptide prepulse assay.

| Peptide | Sequence | $E^k$ | $E^d$ |
|---|---|---|---|
| NONE | | 1.0 | 1.0 |
| AE381 | LRMKLPK (SEQ ID NO:23) | 0.3 | 1.0 |
| AE382 | LRMKLPK (SEQ ID NO:23) | 3.2 | 1.7 |
| AE114 | Ac-LRMKLPK-NH$_2$ (SEQ ID NO:23) | 2.0 | 6.0 |
| AE235 | Ac-LRMKYPK-NH$_2$ (SEQ ID NO:92) | 2.1 | 15.6 |
| AE206 | Ac-LRLKLPK-NH$_2$ (SEQ ID NO:70) | 2.7 | 5.0 |
| AE117 | Ac-YRMK-NH$_2$ (SEQ ID NO:26) | 2.3 | 4.4 |
| AE366 | Ac-LR Harg KYP Cit-NH$_2$ (SEQ ID NO:154) | 3.5 | 7.5 |
| AE172 | Ac-LRMKlpk-NH$_2$ (SEQ ID No:123) | 2.1 | 1.1 |
| AE230 | Ac-LRMKDPK-NH$_2$ (SEQ ID NO:87) | 1.6 | 0.8 |
| AE331 | Ac-LRMK(X14)PK-NH$_2$ (SEQ ID NO:159) | 1.2 | 1.3 |
| AE332 | Ac-LRMK(X15)PK-NH$_2$ (SEQ ID NO:159) | 2.5 | 1.7 |

Table 35: Activities of multiple substitution analogs of AE235, targeting the $E^k$ and $E^d$ allele, in an AE101 series peptide prepulse assay. In this assay the concentration of AE101 series peptides used during the prepulse was 64 μM. The concentrations of antigenic peptides were 0.3 μM for $E^d$ and 0.4 μM for $E^k$. The supernatant dilutions taken into the HT-2 cell assay was 1:4 for $E^d$ and 1:2 for $E^k$. The AE381 peptide is a head-to-tail cyclization: the amino terminal amino group is coupled through an amide linkage to the carboxyl terminal group. The AE 382 peptide is a side-to-tail cyclization: the epsilon amino group of Lys$^4$ is coupled through an amide linkage to the carboxyl terminal group.

AE101 series peptide prepulse assays were carried out in the Ed and Ek systems as described for simultaneous competition assays with the following modifications. Fixed APC were first incubated for 6 h at 1×10$^6$DMEM-5% FCS with 64 μM of each AE101 series peptide or with PBS. The APC were then washed four times with ten volumes of DMEM-5% FCS, and were cocultured with T hybridoma cells and the indicated submaximal doses of antigenic peptides used in the simultaneous competition assays. The baseline T cell response was measured by culturing T hybridoma cells with antigenic peptide and PBS-pretreated APC.

The results of this assay demonstrate that the low activity of AE381 (cyclic LRMKLPK) in the simultaneous assay (Example 1, Table 18) and its potent activities in the antigenic peptide prepulse assay (Example 5, Table 28) and in the processed antigen assay (Example 6, Table 34) are paralleled by its potent suppressive activity in the AE101 series peptide prepulse assay. These sets of data support the view that AE381 binds tightly to the allosteric effector site, without allowing for the substitution of the antigenic peptide at the antigenic peptide binding site by a second antigenic peptide.

Example 7

Mechanisms of AE101 series compound-induced release of human myelin basic protein (hMBP) peptide (90-102) from the antigenic peptide binding site of HLA-DR1 molecules Four assays with purified HLA-DR1 molecules were established to determine the molecular mechanisms of AE101 series compounds with respect to binding, release, or exchange of antigenic peptides at their binding site in MHC class II molecules. These experiments define parameters for the most effective therapeutic use of individual AE101 series compounds.

The four assays measure the following. (I) The effect of AE101 series compounds to release a biotinylated antigenic peptide from the antigenic peptide binding site, without the concerted effect of a second, unlabeled antigenic peptide to promote release of the biotinylated antigenic peptide. (II) The effect of AE101 series compounds to release a biotinylated antigenic peptide from the antigenic peptide binding site, with a second, unlabeled antigenic peptide promoting release of the biotinylated antigenic peptide. (III) The effect of AE101 series compounds to promote the binding of a biotinylated antigenic peptide into MHC class II molecules which have already been loaded with a second, antigenic peptide. (IV) The effect of AE101 series compounds to promote the binding of a biotinylated antigenic peptide into an antigenic peptide binding site of MHC class II molecules which have not been loaded with a second, antigenic peptide. With respect to these last two assays, it is relevant to note that the MHC class II molecules which were prepared for these assays were synthesized in cultured insect cells which were infected with an insect virus carrying the genes for the human MHC class II molecules. These human MHC class II proteins are produced in the cultured insect cells without any peptides occupying the antigenic peptide binding site (Stern, L. J., and Wiley, D. C., *Cell* 68: 465–477, (1992)).

These assays were performed with a soluble form of the MHC class II molecule which is truncated as an exomembranal construct. A peptide sequence was added to the C-terminus of the MHC class II alpha chain, so that the heterodimeric MHC class II alpha, beta chain complex could be tethered in the assay well by a monoclonal antibody to that peptidyl "tail" without apparently affecting the conformational changes in MHC class II molecules induced by AE101 compounds. Elimination of the hydrophobic, transmembranal segments of each chain of the receptor reduces substantial background binding of certain assay components. Putting the "tail" on the alpha chain rather than on the beta chain is preferred because little genetic polymorphism of the alpha chain is found in humans, while there is great polymorphism of the beta chain. Inherited susceptibility to certain autoimmune diseases is linked to some beta chain forms. In 25 future studies of drug design to control such diseases on a MHC Class II allele-specific basis, it will be convenient to construct multiple assay complexes with the constant, "tailed", truncated alpha chain and various truncated forms of beta chains without such tails. Designing this assay with the "tail" on only the alpha chain is thus a preferred characteristic.

Certain constructs of the genes for the HLA-DR alpha and beta chains of the MHC class II molecules were prepared. The HLA-DR alpha gene was truncated after $Asn^{192}$ to remove transmembranal and cytoplasmic regions from the protein product. Codons for a nine amino acid HA epitope were attached to the gene for the alpha chain after the codon for $Asn^{192}$ to permit binding of the modified protein product by a monoclonal antibody 12CA5 (Kolodziej, P. A., and Young, R. A., *Methods Enzymol.* 194: 508–519 (1991)). A gene coding for the HLA-DR1 beta chain was truncated after position $Lys^{198}$, again to delete the transmembranal region. Each gene was cloned into a respective Baculovirus (BV) by standard molecular biological 10 methods. The insect cell line H5 (Invitrogen) was co-infected with the two, respective, purified BV-HLA-DR alpha and BV-HLA-DR1 beta clones. Three days after co-infection, the supernatant of the H5 cell culture was brought to 1 mM iodoacetamide, 1 mM phenylmethylsulfonyl fluoride, and 1 mM ethylenediaminetetraacetic acid (EDTA), and was collected and concentrated 10–15 times by ultrafiltration over an Amicon YM30 membrane.

The general form of the biotinylated antigenic peptide release assay was performed as follows. The wells of a 96-well microtiter plate were coated with the 12CA5 anti-HA tail antibody (2.5 µg/mL in 50 mM sodium carbonate, pH 9.6) at 4° C. overnight Those coated microtiter wells were then blocked with bovine gelatin (2 mg/mL) for 3–5 h at 4° C. Concentrated H5 cell culture supernatant (100 µl) was added to each well and the plates were incubated at 4° C. for 2 h. N-terminally biotin-labeled hMBP(90-102) (50 µM/75 µl) in PBS with 0.02% sodium azide and 1 mM EDTA was added to each well and the plates were incubated at 37° C. overnight. After washing with 0.05% Tween in PBS (100 µl), AE100 series compounds in PBS with 0.02% sodium azide and 1 mM EDTA were added at indicated concentrations and the plates were incubated at 37° C. for 1 h. After washing, avidin-conjugated horseradish peroxidase (HRP) was added and incubated at 4° C. for 1 h. After washing, 100 µl of HRP substrate 3,3',5,5',-tetramethylbenzidine (sigma) was added to each well and the plates were incubated at room temperature for 5 min. 25 µl of 2N sulfuric acid was added to each well to stop the reaction. The colorimetric change at 450 nm was quantitated with an ELISA reader (Molecular Devices). Each value was the average of duplicates and each observations was made at least twice. Comparable results were obtained in initial experiments with biotin-labeled influenza virus hemagglutinin peptide (307-319) (PKYVKQNTLKLAT) (SEQ ID NO:164), and with influenza virus matrix peptide (18-29) (GPLKAEIAQRLE) (SEQ ID NO:165) both of which have also been shown to bind to HLA-DR1. The specific variations for three additional assays are presented in the legend of each Table.

I. Induction of release of hMBP(90-102) from HLA-DR1 by some AE101 series compounds.

In Table 36, it is apparent that some AE101 compounds completely release biotin-labeled hMBP(90-102) from DR1 molecules. Some other compounds, which were very effective in murine in vitro assays for antigen presentation, did not effectively release biotinylated hMBP(90-102). For example, AE235 peptide, which was effective in various murine MHC class II in vitro assays for the presentation of specific antigenic peptides by antigen presenting cells to their respective T cell hybridomas, did not release bound antigenic peptide hMBP(90-102) from HLA-DR1 while some other, longer AE101 series compounds did. The motif of residues in AE101 series compounds required for release of biotinylated antigenic peptides without the presence of a second unlabeled antigenic peptide was determined. Among a series of homologs, the N-terminal 12 amino acid peptide AE107 but not the N-terminal 10 amino acid peptide AE108 released biotin-labeled hMBP(90-102) from the HLA-DR1 molecules, indicating that AE108 did not contain amino acids which played a role in releasing hMBP(90-102) from HLA-DR1 molecules. The N-terminal portion of AE100, AE401, however, retained capacity to release the hMBP(90-102) peptide from HLA-DR1 molecules. In additional experiments, AE101, AE106, and AE107 at 125 nM completely release hMBP(90-102) from HLA-DR1 under the conditions of this assay.

TABLE 36

Induction of release of hMBP(90-102) from HLA-DR1 by some AE101 series compounds.

| Peptide AE# | Sequence | Relative Release |
|---|---|---|
| Pos. Control | | 1.00 |
| Neg. Control | | 0.00 |
| AE101 | YRMKLPKSAKPVSQMR (SEQ ID NO:3) | −0.33 |
| AE106 | YRMKLPKSAKPVSQ (SEQ ID NO:14) | −0.12 |
| AE107 | YRMKLPKSAKPV (SEQ ID NO:15) | −0.07 |
| AE108 | YRMKLPKSAK (SEQ ID NO:16) | 1.14 |
| AE103 | KLPKSAKPVSQMR (SEQ ID NO:11) | 0.01 |
| AE104 | PKSAKPVSQMR (SEQ ID NO:12) | 0.02 |
| AE105 | SAKPVSQMR (SEQ ID NO:13) | 0.16 |
| AE100 | YRMKLPKPPKPVSKMR (SEQ ID NO:2) | 0.37 |
| AE401 | Ac-LRMKLPKPP-NH$_2$ (SEQ ID NO:160) | 0.16 |
| AE402 | Ac-LRMKLPKPPKPV-NH$_2$ (SEQ ID NO:161) | 0.65 |
| AE403 | Ac-MKLPKPPKPV-NH$_2$ (SEQ ID NO:162) | 0.64 |
| AE405 | Ac-LPKSAKPV-NH$_2$ (SEQ ID NO:163) | 0.11 |
| AE235 | Ac-LRMKYPK-NH$_2$ (SEQ ID NO:92) | 0.79 |

Table 36. Induction of release of hMBP(90-102) from HLA-DR1 by some AE101 series compounds. AE101 series compounds were tested at 64 µM. The positive control wells contained only PBS without an AE101 series compound. The positive control value was set at 1.0. The negative control wells contained supernatant of H5 cells infected with wild type Baculovirus and then biotin-labeled hMBP was added. The negative control value was set at 0.0. Relative release of biotinylated antigenic peptide was expressed as the fraction the o.d. of the experimental value was of the o.d. of the positive control value.

II. The release of antigenic peptides from HLA-DR1 complexes is catalyzed by certain AE101 series compounds only in the presence of unlabeled antigenic peptide.

While some AE compounds effectively release bound biotin-labeled hMBP(90-102), some other AE101 series compounds can not. Those later AE101 series compounds were then tested for release of hMBP(90-120) in the presence of excess unlabeled hMBP. In the presence of excess unlabeled hMBP(90-120), some AE101 series compounds, which do not release antigenic peptide from DR molecules in the absence of excess unlabeled hMBP(90-120), can effectively release bound hMBP effectively in the presence of excess unlabeled hMBP(90-120).

TABLE 37

Release of antigenic peptides from HLA-DR1 complexes catalyzed by certain AE101 series compounds only in the presence of unlabeled antigenic peptide.

| | | Relative Release | | | |
|---|---|---|---|---|---|
| | | Without unlabeled hMBP(90-102) | | With unlabeled hMBP(90-102) | |
| Peptide AE# | Sequence | 1 µM | 64 µM | 1 µM | 64 µM |
| AE381 | cyclic LRMKLPK (SEQ ID NO:23) | 0.64 | 0.5 | 0.09 | −0.19 |
| AE206 | Ac-LRLKLPK-NH$_2$ (SEQ ID NO:70) | 0.58 | 0.08 | 0.03 | −0.29 |
| AE108 | YRMKLPKSAK (SEQ ID NO:16) | 0.52 | 0.31 | 0.00 | 0.14 |
| AE143 | Ac-YRMKLhydrpKSAK-NH$_2$ (SEQ ID NO:94) | 0.51 | 0.58 | 0.35 | 0.21 |
| AE235 | Ac-LRMKYPK-NH$_2$ (SEQ ID NO:92) | 1.05 | 0.81 | 0.48 | 0.6 |

Table 37. Some AE101 series compounds catalyze the release of biotin-labeled hMBP(90-102) from HLA-DR1 molecules only in the presence of unlabeled hMBP. AE101 series compounds were tested at 1 µM and at 64 µM. The experimental procedures were the same as reported for Table M1, except that unlabeled hMBP(90-102) (250 µM) was added in some wells during the release-inducing step, as indicated. Release of biotin-labeled hMBP(90-102) by unlabeled hMBP(90-102) alone without AE101 series compounds was 0.81, and release of biotin-labeled hMBP(90-102) by AE101 at 1 µM without hMBP(90-102) was 0.02. The presence of unlabeled antigenic peptide in the solution greatly enhanced the release of biotinylated antigenic peptide by certain AE101 series compounds.

III. Certain AE101 series compounds exchange biotinylated antigenic peptides into antigenic peptide-loaded HLA-DR molecules.

Some AE101 compounds were found to release bound antigenic peptide from MHC class II molecules in the presence of excess unlabeled antigenic peptide. Next, the activity of AE101 series compounds to promote the exchange of the antigenic peptide with respect to MHC class II molecules was tested. Certain AE101 series compounds promote the exchange of antigenic peptides with respect to MHC class II molecules. AE101 series compounds with this activity usually also had the ability to release antigenic peptides from the MHC class II molecules.

TABLE 38

Certain AE101 series compounds exchange hMBP(90-102) into HLA-DR1 molecules.

| Peptide AE# | Sequence | Relative Binding |
|---|---|---|
| Pos. Control | | 1.00 |
| Neg. Control | | 0.00 |
| No enhancement | | 0.08 |
| AE101 | YRMKLPKSAKPVSQMR (SEQ ID NO:3) | 0.31 |
| AE107 | YRMKLPKSAKPV (SEQ ID NO:15) | 1.04 |
| AE381 | cyclic LRMKLPK (SEQ ID NO:23) | −0.12 |
| AE206 | Ac-LRLKLPK-NH$_2$ (SEQ ID NO:70) | −0.13 |
| AE100 | YRMKLPKPPKPVSKMR (SEQ ID NO:2) | 0.31 |

TABLE 38-continued

Certain AE101 series compounds exchange hMBP(90-102) into HLA-DR1 molecules.

| Peptide AE# | Sequence | Relative Binding |
|---|---|---|
| AE401 | Ac-LRMKLPKPP-NH$_2$ (SEQ ID NO:160) | 0.45 |
| AE402 | Ac-LRMKLPKPPKPV-NH$_2$ (SEQ ID NO:161) | −0.03 |
| AE403 | Ac-MKLPKPPKPV-NH$_2$ (SEQ ID NO:162) | 0.40 |
| AE405 | Ac-LPKSAKPV-NH$_2$ (SEQ ID NO:163) | 0.57 |
| AE235 | Ac-LRMKYPK-NH$_2$ (SEQ ID NO:92) | 0.15 |

Table 38. Certain AE101 series compounds exchange biotinylated hMBP(90-102) into antigenic peptide-loaded HLA-DR1 molecules. The experimental procedures were the same as described in Table M1 except that unlabeled hMBP(90-102) (50 μM) was first incubated with purified, soluble HLA-DR1 molecules overnight, and the cells were then washed. The exchange step was then performed with AE101 series compounds in the presence of biotin-labeled hMBP(90-102) (50 μM) at 37° C. for 1 h. The positive control was the HLA-DR molecules incubated with biotin-labeled hMBP(90-102) (50 μM) overnight. The negative control was wild type supernatant incubated with biotin-labeled hMBP(90-102). "No enhancement" refers to the performance of the exchange step in the presence of biotin-labeled hMBP(90-102) (50 μM) without AE101 series compounds at 37° C. for 1 h. Relative binding was the fraction the o.d. of the experimental value was of the o.d. of the positive control value.

IV. Certain AE compounds promote the binding of antigenic peptide to "empty" HLA-DR molecules.

This experiment addressed whether AE101 series compounds might induce a conformational change in the nascent, "empty" MHC class II molecules to facilitate binding of antigenic peptide to MHC class II molecules.

Insect cell-produced HLA-DR1 molecules are known to be empty (Stern, L. J., and Wiley, D. C., Cell 68:465–477, 1992). Some AE101 series compounds promoted the binding of hMBP to HLA-DR1 molecules. This finding indicated that AE101 series compounds induced a conformational change favoring the binding of hMBP.

TABLE 39

AE101 Series compounds promote the binding of hMBP(90-102) to "empty" HLA-DR1 molecules.

| Peptide AE# | Sequence | Relative Enhancement |
|---|---|---|
| No enhancement | | 1 |
| Neg. control | | 0.00 |
| AE101 | YRMKLPKSAKPVSQMR (SEQ ID NO:3) | 2.66 |
| AE107 | YRMKLPKSAKPV (SEQ ID NO:15) | 2.59 |
| AE381 | cyclic LRMKLPK (SEQ ID NO:23) | 1.84 |
| AE206 | Ac-LRLKLPK-NH$_2$ (SEQ ID NO:70) | 2.57 |
| AE100 | YRMKLPKPPKPVSKMR (SEQ ID NO:2) | 3.44 |
| AE401 | Ac-LRMKLPKPP-NH$_2$ (SEQ ID NO:160) | 4.29 |

TABLE 39-continued

AE101 Series compounds promote the binding of hMBP(90-102) to "empty" HLA-DR1 molecules.

| Peptide AE# | Sequence | Relative Enhancement |
|---|---|---|
| AE402 | Ac-LRMKLPKPPKPV-NH$_2$ (SEQ ID NO:161) | 0.33 |
| AE403 | Ac-MKLPKPPKPV-NH$_2$ (SEQ ID NO:162Y) | 0.47 |
| AE405 | Ac-LPKSAKPV-NH$_2$ (SEQ ID NO:163) | 0.43 |
| AE235 | Ac-YRMKYPK-NH$_2$ (SEQ ID NO:92) | 0.61 |

Table 39. Certain AE101 series compounds promote the binding of biotin-labeled hMBP(90-102) to "empty" HLA-DR1 molecules. After HLA-DR1 molecules were immobilized onto the plate, the wells were washed 3 times with 0.05% Tween in PBS. They were then incubated biotin-labeled hMBP(90-102) (50 μM) in PBS with 1 mM EDTA and the indicated AE101 series compound (64 μM) at 37° C. for 1 h. The wells were washed and developed with avidin conjugated HRP, followed by a colorimetric assay. Relative enhancement was the fraction the o.d. of the experimental value was of the o.d. of the positive control value. No enhancement was the value seen with the HLA-DR1 molecules incubated with biotin-labeled hMBP(90-102) without the AE101 series compound at 37° C. for 1 h and was set at 1.0. The negative control was with supernatant of a culture with wild type Baculovirus with biotin-labeled hMBP(90-102) at 37° C. for 1 h. That value was set at 0.0.

Data of this Example reveal three classes or groups of AE101 series compounds which can be identified in terms of their differing activities to release, to exchange and/or to promote the binding of antigenic peptides with respect to HLA-DR1 molecules. These three activity classes, which also relate to the structures of the compounds, lead to a molecular mechanism model which is consistent with two x-ray crystallographic studies of peptide binding into the antigenic peptide binding site of MHC class II molecules. The three, empirical patterns of activity are the following.

1) Group One. Certain AE101 series compounds efficiently release bound antigenic peptide from HLA-DR1 molecules in the absence of additional antigenic peptide. They also efficiently replace bound antigenic peptide with a second unbound antigenic peptide. Since these compounds also promote the initial binding of antigenic peptide to freshly prepared, "empty" DR1 molecules, as synthesized in the insect virus/cell line system, they appear to induce a conformational change in such DR1 molecules to promote or permit initial binding of antigenic peptides.

2) Group Two. Other AE101 series compounds cannot efficiently release bound antigenic peptide from HLA-DR1 molecules in the absence of unlabeled antigenic peptide, and release bound antigenic peptide but only in the presence of excess unlabeled antigenic peptide. This subset of AE101 series compounds does not efficiently promote the binding of antigenic peptides to nascent HLA-DR1 molecules.

3) Group Three. Yet other AE101 series compounds demonstrate little activity in releasing, exchanging, or promoting the binding of antigenic peptides to HLA-DR1 molecules.

Assignment of individual AE101 series compounds to each of these three classes might vary depending upon the MHC class II alleles and the species being studied in a given screening assay. In the studies of this disclosure, various AE101 series compounds demonstrate significant degrees of allele and species specificity.

The data of this disclosure indicate varying molecular mechanisms by which AE101 series compounds release or promote the binding of antigenic peptides to MHC class II molecules. These mechanisms can be interpreted in terms of ways in which AE101 series compounds might bind to a different binding site than where antigenic peptides bind to MHC class II molecules, that is, to an allosteric site. The binding of AE101 series compounds to such an allosteric regulatory site appears to loosen the antigenic peptide binding site to release antigenic peptide and to promote the binding of antigenic peptide. From the functional data alone one might propose that Group One AE101 series compounds might open the antigenic peptide completely so that the MHC class II molecules can release, exchange, and promote the charging of second antigenic peptides. Group Two AE101 series compounds appear only partially to open the antigenic peptide binding site. Such a limited action loosens the bound antigenic peptide but an additional force, such as that induced by the binding of a second antigenic peptide, is required for the substitution of the first antigenic peptide.

These hypothesized molecular mechanisms can be related to certain structural specifications for each of the AE101 series compounds. These mechanisms also relate to the crystallographic images of certain peptides bound to MHC class II molecules, containing either antigenic peptide or the Ii protein-derived "CLIP" peptide (Stern et al., *Nature* 368: 215–221 (1994) and Ghosh et al., *Nature* 378: 457–462 (1995)). First, it was observed that certain AE101 series compounds comprising homologs of up to the 10 N-terminal amino acids of the AE101 peptide catalyze the release of biotinylated antigenic peptide from the antigenic peptide binding site only in the presence in solution of additional antigenic peptide. Without the presence of that additional antigenic peptide, these 10 amino acid or less homologs of AE101 presumably only bind to the MHC class II molecule. Secondly, it was observed that AE101 series compounds comprising homologs of 12 or more of the amino acids from the N-terminus of AE101, or better yet running from positions $Leu^5$ to $Val^{12}$ in AE101, induce the dissociation of bound antigenic peptide from the antigenic peptide binding site of MHC class II molecules without the requirement for additional antigenic peptide being present in the solution. The motif required for this autocatalytic effect on release of antigenic peptides, thus, did not extend to the N-terminus of the AE101 peptide since the residues of AE405, comprising residue positions 5 through 12 of AE101, were sufficient to release antigenic peptide without the presence of excess quantities in solution of a second antigenic peptide. In light of the crystallographic data of Stern et al. and Ghosh et al., one can propose that, if the Ii protein lies in MHC class II molecules in registry with the positioning of the CLIP peptide of Ii within the antigenic peptide binding site and the AE101 series compounds lie in registry with that hypothesized positioning of the Ii protein, then the following subsites can be identified. First, there is the antigenic peptide binding trough extending C-terminally from $p^{85}$ in Ii (P6 in AE101 peptide). Secondly, there is a core of the AE101 structure represented by AE114 which can catalyze the release of antigenic peptide from the antigenic peptide binding site only in the presence of excess quantities of a second antigenic peptide. Thirdly, there is a subsite ranging from $P^5$ through $V^{12}$ (partially overlapping the second allosteric effector site) which is sufficient to exchange antigenic peptide from the antigenic peptide binding site.

SEQUENCE LISTING (1) GENERAL INFORMATION:

(iii) NUMBER OF SEQUENCES: 165

(2) INFORMATION FOR SEQ ID NO:1:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
   Leu Arg Met Lys Leu Pro Lys Pro Pro Lys Pro Val Ser Lys Met Arg
   1               5                  10                  15
```

(2) INFORMATION FOR SEQ ID NO:2:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

```
   Tyr Arg Met Lys Leu Pro Lys Pro Pro Lys Pro Val Ser Lys Met Arg
   1               5                  10                  15
```

(2) INFORMATION FOR SEQ ID NO:3:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Tyr Arg Met Lys Leu Pro Lys Ser Ala Lys Pro Val Ser Gln Met Arg
 1               5                  10                  15
```

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Leu Arg Met Lys Leu Pro Lys
 1               5
```

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Ala Met Lys Arg His Gly Leu Asp Asn Tyr Arg Gly Tyr Ser Leu
 1               5                  10                  15
```

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Asn Thr Asp Gly Ser Thr Asp Tyr Gly Ile Leu Gln Ile Asn Ser Arg
 1               5                  10                  15
```

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Asn Ala Trp Val Ala Trp Arg Asn Arg Cys Lys
 1               5                  10
```

(2) INFORMATION FOR SEQ ID NO:8:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Ile Phe Ala Gly Ile Lys Lys Ala Glu Arg Ala Asp Leu Ile Ala
1               5                  10                  15

Tyr Leu Lys Gln Ala Thr Ala Lys
            20
```

(2) INFORMATION FOR SEQ ID NO:9:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Phe Ala Gly Leu Lys Lys Ala Asn Glu Arg Ala Asp Leu Ile Ala Tyr
1               5                  10                  15

Leu Lys Gln Ala Thr Lys
            20
```

(2) INFORMATION FOR SEQ ID NO:10:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Arg Met Lys Leu Pro Lys Ser Ala Lys Pro Val Ser Gln Met Arg
1               5                  10                  15
```

(2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Lys Leu Pro Lys Ser Ala Lys Pro Val Ser Gln Met Arg
1               5                  10
```

(2) INFORMATION FOR SEQ ID NO:12:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Pro Lys Ser Ala Lys Pro Val Ser Gln Met Arg
    1               5                  10

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Ser Ala Lys Pro Val Ser Gln Met Arg
    1               5

(2) INFORMATION FOR SEQ ID NO:14:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Tyr Arg Met Lys Leu Pro Lys Ser Ala Lys Pro Val Ser Gln
    1               5                  10

(2) INFORMATION FOR SEQ ID NO:15:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Tyr Arg Met Lys Leu Pro Lys Ser Ala Lys Pro Val
    1               5                  10

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Tyr Arg Met Lys Leu Pro Lys Ser Ala Lys
    1               5                  10

(2) INFORMATION FOR SEQ ID NO:17:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Leu Arg Met Lys Leu Pro Lys Ser Ala Lys
   1               5                   10

(2) INFORMATION FOR SEQ ID NO:18:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:18:

Leu Arg Met Lys Leu Pro Lys Pro Pro Pro
   1               5                   10

(2) INFORMATION FOR SEQ ID NO:19:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:19:

Leu Arg Met Lys Leu Pro Lys Pro Pro Lys
   1               5                   10

(2) INFORMATION FOR SEQ ID NO:20:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:20:

Tyr Arg Met Lys Leu Pro Lys Ser Ala
   1               5

(2) INFORMATION FOR SEQ ID NO:21:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:21:

Tyr Arg Met Lys Leu Pro Lys Ser
   1               5

(2) INFORMATION FOR SEQ ID NO:22:

(i) SEQUENCE CHARACTERISTICS:
       (A) LENGTH: 7 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:22:

Tyr Arg Met Lys Leu Pro Lys
   1               5

(2) INFORMATION FOR SEQ ID NO:23:

(i) SEQUENCE CHARACTERISTICS:
       (A) LENGTH: 7 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:23:

Leu Arg Met Lys Leu Pro Lys
   1               5

(2) INFORMATION FOR SEQ ID NO:24:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:24:

Tyr Arg Met Lys Leu Pro
   1               5

(2) INFORMATION FOR SEQ ID NO:25:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:25:

Tyr Arg Met Lys Leu
   1               5

(2) INFORMATION FOR SEQ ID NO:26:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:26:

Tyr Arg Met Lys
   1

(2) INFORMATION FOR SEQ ID NO:27:

(i) SEQUENCE CHARACTERISTICS:
       (A) LENGTH: 3 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:27:

Tyr Arg Met
1

(2) INFORMATION FOR SEQ ID NO:28:

(i) SEQUENCE CHARACTERISTICS:
　　(A) LENGTH: 11 amino acids
　　(B) TYPE: amino acid
　　(C) STRANDEDNESS: single
　　(D) TOPOLOGY: linear (ii) MOLECULE TYPE: peptide (xi) SEQUENCE DESCRIPTION: SEQ ID NO:28:

Ser Leu Arg Met Lys Leu Pro Lys Ser Ala Lys
1               5                   10

(2) INFORMATION FOR SEQ ID NO:29:

(i) SEQUENCE CHARACTERISTICS:
　　(A) LENGTH: 12 amino acids
　　(B) TYPE: amino acid
　　(C) STRANDEDNESS: single
　　(D) TOPOLOGY: linear (ii) MOLECULE TYPE: peptide (xi) SEQUENCE DESCRIPTION: SEQ ID NO:29:

Asp Ser Leu Arg Met Lys Leu Pro Lys Ser Ala Lys
1               5                   10

(2) INFORMATION FOR SEQ ID NO:30:

(i) SEQUENCE CHARACTERISTICS:
　　(A) LENGTH: 13 amino acids
　　(B) TYPE: amino acid
　　(C) STRANDEDNESS: single
　　(D) TOPOLOGY: linear (ii) MOLECULE TYPE: peptide (xi) SEQUENCE DESCRIPTION: SEQ ID NO:30:

Leu Asp Ser Leu Arg Met Lys Leu Pro Lys Ser Ala Lys
1               5                   10

(2) INFORMATION FOR SEQ ID NO:31:

(i) SEQUENCE CHARACTERISTICS:
　　(A) LENGTH: 14 amino acids
　　(B) TYPE: amino acid
　　(C) STRANDEDNESS: single
　　(D) TOPOLOGY: linear (ii) MOLECULE TYPE: peptide (xi) SEQUENCE DESCRIPTION: SEQ ID NO:31:

Gln Leu Asp Ser Leu Arg Met Lys Leu Pro Lys Ser Ala Lys
1               5                   10

(2) INFORMATION FOR SEQ ID NO:32:

(i) SEQUENCE CHARACTERISTICS:
　　(A) LENGTH: 15 amino acids
　　(B) TYPE: amino acid
　　(C) STRANDEDNESS: single
　　(D) TOPOLOGY: linear (ii) MOLECULE TYPE: peptide (xi) SEQUENCE DESCRIPTION: SEQ ID NO:32:

Leu Gln Leu Asp Ser Leu Arg Met Lys Leu Pro Lys Ser Ala Lys
   1             5                   10              15

(2) INFORMATION FOR SEQ ID NO:33:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:33:

Asn Leu Gln Leu Asp Ser Leu Arg Met Lys Leu Pro Lys Ser Ala Lys
   1             5                   10              15

(2) INFORMATION FOR SEQ ID NO:34:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (D) OTHER INFORMATION: /note= "The Xaa at position 1 is Orn."

(xi) SEQUENCE DESCRIPTION: SEQ ID NO:34:

Xaa Arg Met Lys Leu Pro Lys
   1             5

(2) INFORMATION FOR SEQ ID NO:35:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (D) OTHER INFORMATION: /note= "The Xaa at position 1 is Cit."

(xi) SEQUENCE DESCRIPTION: SEQ ID NO:35:

Xaa Arg Met Lys Leu Pro Lys
   1             5

(2) INFORMATION FOR SEQ ID NO:36:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (D) OTHER INFORMATION: /note= "The Xaa at position 1 is HArg."

(xi) SEQUENCE DESCRIPTION: SEQ ID NO:36:

```
    Xaa Arg Met Lys Leu Pro Lys
    1               5
```

(2) INFORMATION FOR SEQ ID NO:37:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

```
    His Arg Met Lys Leu Pro Lys
    1               5
```

(2) INFORMATION FOR SEQ ID NO:38:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

```
    Lys Arg Met Lys Leu Pro Lys
    1               5
```

(2) INFORMATION FOR SEQ ID NO:39:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
    Asp Arg Met Lys Leu Pro Lys
    1               5
```

(2) INFORMATION FOR SEQ ID NO:40:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

```
    Glu Arg Met Lys Leu Pro Lys
    1               5
```

(2) INFORMATION FOR SEQ ID NO:41:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

```
    Asn Arg Met Lys Leu Pro Lys
    1               5
```

(2) INFORMATION FOR SEQ ID NO:42:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

```
    Gln Arg Met Lys Leu Pro Lys
    1               5
```

(2) INFORMATION FOR SEQ ID NO:43:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

```
    Phe Arg Met Lys Leu Pro Lys
    1               5
```

(2) INFORMATION FOR SEQ ID NO:44:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

```
    Met Arg Met Lys Leu Pro Lys
    1               5
```

(2) INFORMATION FOR SEQ ID NO:45:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

```
    Tyr Ala Met Lys Leu Pro Lys Ser Ala Lys
    1               5                   10
```

(2) INFORMATION FOR SEQ ID NO:46:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
        Tyr Arg Asn Met Lys Leu Pro Lys Ser Ala Lys
        1               5                   10
```

(2) INFORMATION FOR SEQ ID NO:47:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 2 is Cit."

(xi) SEQUENCE DESCRIPTION: SEQ ID NO:47:

```
        Tyr Xaa Met Lys Leu Pro Lys Ser Ala Lys
        1               5                   10
```

(2) INFORMATION FOR SEQ ID NO:48:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 2 is HArg."

(xi) SEQUENCE DESCRIPTION: SEQ ID NO:48:

```
        Tyr Xaa Met Lys Leu Pro Lys Ser Ala
        1               5
```

(2) INFORMATION FOR SEQ ID NO:49:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

```
        His Met Lys Leu Pro Lys Ser Ala Lys
        1               5
```

(2) INFORMATION FOR SEQ ID NO:50:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

```
        Tyr Lys Met Lys Leu Pro Lys Ser Ala Lys
        1               5                   10
```

(2) INFORMATION FOR SEQ ID NO:51:

(i) SEQUENCE CHARACTERISTICS:
        (A) LENGTH: 10 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:51:

Tyr Asp Met Lys Leu Pro Lys Ser Ala Lys
        1               5                   10

(2) INFORMATION FOR SEQ ID NO:52:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:52:

Tyr Glu Met Lys Leu Pro Lys Ser Ala Lys
        1               5                   10

(2) INFORMATION FOR SEQ ID NO:53:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:53:

Tyr Asn Met Lys Leu Pro Lys Ser Ala Lys
        1               5                   10

(2) INFORMATION FOR SEQ ID NO:54:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:54:

Tyr Gln Met Lys Leu Pro Lys Ser Ala Lys
        1               5                   10

(2) INFORMATION FOR SEQ ID NO:55:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:55:

Tyr Phe Met Lys Leu Pro Lys Ser Ala Lys
        1               5                   10

(2) INFORMATION FOR SEQ ID NO:56:

(i) SEQUENCE CHARACTERISTICS:
            (A) LENGTH: 10 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

Tyr Tyr Met Lys Leu Pro Lys Ser Ala Lys
      1               5                   10

(2) INFORMATION FOR SEQ ID NO:57:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

Tyr Met Met Lys Leu Pro Lys Ser Ala Lys
      1               5                   10

(2) INFORMATION FOR SEQ ID NO:58:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

Tyr Leu Met Lys Leu Pro Lys Ser Ala Lys
      1               5                   10

(2) INFORMATION FOR SEQ ID NO:59:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 3 is Orn."

(xi) SEQUENCE DESCRIPTION: SEQ ID NO:59:

Leu Arg Xaa Lys Leu Pro Lys
     1               5

(2) INFORMATION FOR SEQ ID NO:60:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 3 is Cit."

(xi) SEQUENCE DESCRIPTION: SEQ ID NO:60:

Leu Arg Xaa Lys Leu Pro Lys
        1               5

(2) INFORMATION FOR SEQ ID NO:61:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 3 is HArg."

(xi) SEQUENCE DESCRIPTION: SEQ ID NO:61:

Leu Arg Xaa Lys Leu Pro Lys
        1               5

(2) INFORMATION FOR SEQ ID NO:62:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:62:

Leu Arg His Lys Leu Pro Lys
        1               5

(2) INFORMATION FOR SEQ ID NO:63:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

Leu Arg Lys Lys Leu Pro Lys
        1               5

(2) INFORMATION FOR SEQ ID NO:64:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

Leu Arg Asp Lys Leu Pro Lys
        1               5

(2) INFORMATION FOR SEQ ID NO:65:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:65:

Leu Arg Glu Lys Leu Pro Lys
        1               5

(2) INFORMATION FOR SEQ ID NO:66:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

Leu Arg Asn Lys Leu Pro Lys
        1               5

(2) INFORMATION FOR SEQ ID NO:67:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

Leu Arg Gln Lys Leu Pro Lys
        1               5

(2) INFORMATION FOR SEQ ID NO:68:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:68:

Leu Arg Phe Lys Leu Pro Lys
        1               5

(2) INFORMATION FOR SEQ ID NO:69:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:69:

Leu Arg Tyr Lys Leu Pro Lys
        1               5

(2) INFORMATION FOR SEQ ID NO:70:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:70:

Leu Arg Leu Lys Leu Pro Lys
            1               5

(2) INFORMATION FOR SEQ ID NO:71:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (D) OTHER INFORMATION: /note= "The Xaa at position 4 is Orn."

(xi) SEQUENCE DESCRIPTION: SEQ ID NO:71:

Leu Arg Met Xaa Leu Pro Lys
            1               5

(2) INFORMATION FOR SEQ ID NO:72:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (D) OTHER INFORMATION: /note= "The Xaa at position 4 is Cit."

(xi) SEQUENCE DESCRIPTION: SEQ ID NO:72:

Leu Arg Met Xaa Leu Pro Lys
            1               5

(2) INFORMATION FOR SEQ ID NO:73:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (D) OTHER INFORMATION: /note= "The Xaa at position 4 is HArg."

(xi) SEQUENCE DESCRIPTION: SEQ ID NO:73:

Leu Arg Met Xaa Leu Pro Lys
            1               5

(2) INFORMATION FOR SEQ ID NO:74:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:74:

Leu Arg Met His Leu Pro Lys
        1               5

(2) INFORMATION FOR SEQ ID NO:75:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

Leu Arg Met Asp Leu Pro Lys
        1               5

(2) INFORMATION FOR SEQ ID NO:76:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:76:

Leu Arg Met Asp Leu Pro Lys
        1               5

(2) INFORMATION FOR SEQ ID NO:77:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

Leu Arg Met Asn Leu Pro Lys
        1               5

(2) INFORMATION FOR SEQ ID NO:78:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:78:

Leu Arg Met Gln Leu Pro Lys
        1               5

(2) INFORMATION FOR SEQ ID NO:79:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:79:

```
        Leu Arg Met Phe Leu Pro Lys
        1               5
```

(2) INFORMATION FOR SEQ ID NO:80:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:80:

```
        Leu Arg Met Tyr Leu Pro Lys
        1               5
```

(2) INFORMATION FOR SEQ ID NO:81:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:81:

```
        Leu Arg Met Met Leu Pro Lys
        1               5
```

(2) INFORMATION FOR SEQ ID NO:82:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:82:

```
        Leu Arg Met Lys Arg Asn Pro Lys
        1               5
```

(2) INFORMATION FOR SEQ ID NO:83:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 5 is Cit."

(xi) SEQUENCE DESCRIPTION: SEQ ID NO:83:

```
        Leu Arg Met Lys Xaa Pro Lys
        1               5
```

(2) INFORMATION FOR SEQ ID NO:84:

(i) SEQUENCE CHARACTERISTICS:
        (A) LENGTH: 7 amino acids
        (B) TYPE: amino acid
        (C) STRANDEDNESS: single
        (D) TOPOLOGY: linear

```
        (ii) MOLECULE TYPE: peptide (ix) FEATURE:
             (A) NAME/KEY: Modified-site
             (D) OTHER INFORMATION: /note= "The Xaa at position 5 is HArg."

(xi) SEQUENCE DESCRIPTION: SEQ ID NO:84:

Leu Arg Met Lys Xaa Pro Lys
    1               5

(2) INFORMATION FOR SEQ ID NO:85:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:85:

Leu Arg Met Lys His Pro Lys
    1               5

(2) INFORMATION FOR SEQ ID NO:86:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:86:

Leu Arg Met Lys Lys Pro Lys
    1               5

(2) INFORMATION FOR SEQ ID NO:87:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:87:

Leu Arg Met Lys Asp Pro Lys
    1               5

(2) INFORMATION FOR SEQ ID NO:88:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:88:

Leu Arg Met Lys Glu Pro Lys
    1               5

(2) INFORMATION FOR SEQ ID NO:89:

(i) SEQUENCE CHARACTERISTICS:
             (A) LENGTH: 7 amino acids
```

(B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:89:

Leu Arg Met Lys Asn Pro Lys
        1               5

(2) INFORMATION FOR SEQ ID NO:90:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:90:

Leu Arg Met Lys Gln Pro Lys
        1               5

(2) INFORMATION FOR SEQ ID NO:91:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:91:

Leu Arg Met Lys Phe Pro Lys
        1               5

(2) INFORMATION FOR SEQ ID NO:92:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:92:

Leu Arg Met Lys Tyr Pro Lys
        1               5

(2) INFORMATION FOR SEQ ID NO:93:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:93:

Leu Arg Met Lys Met Pro Lys
        1               5

(2) INFORMATION FOR SEQ ID NO:94:

(i) SEQUENCE CHARACTERISTICS:
            (A) LENGTH: 10 amino acids (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 6 is
            hydrP."

(xi) SEQUENCE DESCRIPTION: SEQ ID NO:94:

Tyr Arg Met Lys Leu Xaa Lys Ser Ala Lys
        1               5                   10

(2) INFORMATION FOR SEQ ID NO:95:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:95:

Leu Arg Met Lys Leu Pro Arg Asn
        1               5

(2) INFORMATION FOR SEQ ID NO:96:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 7 is Cit."

(xi) SEQUENCE DESCRIPTION: SEQ ID NO:96:

Leu Arg Met Lys Leu Pro Xaa
        1               5

(2) INFORMATION FOR SEQ ID NO:97:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 7 is HArg."

(xi) SEQUENCE DESCRIPTION: SEQ ID NO:97:

Leu Arg Met Lys Leu Pro Xaa
        1               5

(2) INFORMATION FOR SEQ ID NO:98:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:98:

Leu Arg Met Lys Leu Pro His
            1               5

(2) INFORMATION FOR SEQ ID NO:99:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:99:

Leu Arg Met Lys Leu Pro Asp
            1               5

(2) INFORMATION FOR SEQ ID NO:100:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:100:

Leu Arg Met Lys Leu Pro Glu
            1               5

(2) INFORMATION FOR SEQ ID NO:101:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:101:

Leu Arg Met Lys Leu Pro Asn
            1               5

(2) INFORMATION FOR SEQ ID NO:102:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:102:

Leu Arg Met Lys Leu Pro Gln
            1               5

(2) INFORMATION FOR SEQ ID NO:103:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:103:

Leu Arg Met Lys Leu Pro Phe
        1               5

(2) INFORMATION FOR SEQ ID NO:104:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:104:

Leu Arg Met Lys Leu Pro Tyr
        1               5

(2) INFORMATION FOR SEQ ID NO:105:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

Leu Arg Met Lys Leu Pro Met
        1               5

(2) INFORMATION FOR SEQ ID NO:106:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:106:

Leu Arg Met Lys Leu Pro Leu
        1               5

(2) INFORMATION FOR SEQ ID NO:107:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

Ala Arg Met Lys Leu Pro Lys Ser Ala Lys
        1               5                   10

(2) INFORMATION FOR SEQ ID NO:108:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:108:

```
Tyr Ala Met Lys Leu Pro Lys Ser Ala Lys
1               5                   10
```

(2) INFORMATION FOR SEQ ID NO:109:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:109:

```
Tyr Arg Ala Lys Leu Pro Lys Ser Ala Lys
1               5                   10
```

(2) INFORMATION FOR SEQ ID NO:110:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:110:

```
Tyr Arg Met Ala Leu Pro Lys Ser Ala Lys
1               5                   10
```

(2) INFORMATION FOR SEQ ID NO:111:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:111:

```
Tyr Arg Met Lys Ala Pro Lys Ser Ala Lys
1               5                   10
```

(2) INFORMATION FOR SEQ ID NO:112:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:112:

```
Tyr Arg Met Lys Leu Ala Lys Ser Ala Lys
1               5                   10
```

(2) INFORMATION FOR SEQ ID NO:113:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:113:

```
Tyr Arg Met Lys Leu Pro Ala Ser Ala Lys
1               5                   10
```

(2) INFORMATION FOR SEQ ID NO:114:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:114:

```
Tyr Arg Met Lys Leu Pro Lys Ala Ala Lys
1               5                   10
```

(2) INFORMATION FOR SEQ ID NO:115:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:115:

```
Tyr Arg Met Lys Leu Pro Lys Ser Ala Ala
1               5                   10
```

(2) INFORMATION FOR SEQ ID NO:116:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (D) OTHER INFORMATION: /note= "The Xaa at position 1 is the D-
          amino acid of Leu."

(xi) SEQUENCE DESCRIPTION: SEQ ID NO:116:

```
Xaa Arg Met Lys Leu Pro Lys
1               5
```

(2) INFORMATION FOR SEQ ID NO:117:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (D) OTHER INFORMATION: /note= "The Xaa at position 2 is the D-
          amino acid of Arg."

(xi) SEQUENCE DESCRIPTION: SEQ ID NO:117:

```
    Leu Xaa Met Lys Leu Pro Lys
    1               5
```

(2) INFORMATION FOR SEQ ID NO:118:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 3 is the D-
            amino acid of Met."

(xi) SEQUENCE DESCRIPTION: SEQ ID NO:118:

```
    Leu Arg Xaa Lys Leu Pro Lys
    1               5
```

(2) INFORMATION FOR SEQ ID NO:119:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 4 is the D-
            amino acid of Leu."

(xi) SEQUENCE DESCRIPTION: SEQ ID NO:119:

```
    Leu Arg Met Xaa Leu Pro Lys
    1               5
```

(2) INFORMATION FOR SEQ ID NO:120:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 5 is the D-
            amino acid of Leu."

(xi) SEQUENCE DESCRIPTION: SEQ ID NO:120:

```
    Leu Arg Met Lys Xaa Pro Lys
    1               5
```

(2) INFORMATION FOR SEQ ID NO:121:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 6 is the D-

```
          amino acid of Pro."

(xi) SEQUENCE DESCRIPTION: SEQ ID NO:121:

Leu Arg Met Lys Leu Xaa Lys
       1               5

(2) INFORMATION FOR SEQ ID NO:122:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (D) OTHER INFORMATION: /note= "The Xaa at position 6 is the D-
             amino acid of Lys."

(xi) SEQUENCE DESCRIPTION: SEQ ID NO:122:

Leu Arg Met Lys Leu Pro Xaa
       1               5

(2) INFORMATION FOR SEQ ID NO:123:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (D) OTHER INFORMATION: /note= "The Xaa at position 5 is the D-
             amino acid of Leu, at position 6 is the D-amino acid of
             Pro, and at position 7 is the D-amino acid of Lys."

(xi) SEQUENCE DESCRIPTION: SEQ ID NO:123:

Lys Pro Leu Lys Xaa Xaa Xaa
       1               5

(2) INFORMATION FOR SEQ ID NO:124:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (D) OTHER INFORMATION: /note= "The Xaa at position 6 is the D-
             amino acid of Pro, and at position 7 is the D-amino acid
             of Lys."

(xi) SEQUENCE DESCRIPTION: SEQ ID NO:124:

Leu Arg Met Lys Leu Xaa Xaa
       1               5

(2) INFORMATION FOR SEQ ID NO:125:

(i) SEQUENCE CHARACTERISTICS:
         (A) LENGTH: 7 amino acids
         (B) TYPE: amino acid
         (C) STRANDEDNESS: single
         (D) TOPOLOGY: linear
```

(ii) MOLECULE TYPE: peptide (ix) FEATURE:
    (A) NAME/KEY: Modified-site
    (D) OTHER INFORMATION: /note= "The Xaa at position 1 is N-methyl Leu."

(xi) SEQUENCE DESCRIPTION: SEQ ID NO:125:

Xaa Arg Met Lys Leu Pro Lys
    1            5

(2) INFORMATION FOR SEQ ID NO:126:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (D) OTHER INFORMATION: /note= "The Xaa at position 5 is N-methyl Leu."

(xi) SEQUENCE DESCRIPTION: SEQ ID NO:126:

Leu Arg Met Lys Xaa Pro Lys
    1            5

(2) INFORMATION FOR SEQ ID NO:127:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:127:

Leu Arg Leu Lys Tyr Pro Lys
    1            5

(2) INFORMATION FOR SEQ ID NO:128:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (D) OTHER INFORMATION: /note= "The Xaa at position 3 is N-methyl Leu."

(xi) SEQUENCE DESCRIPTION: SEQ ID NO:128:

Leu Arg Xaa Lys Leu Pro Lys
    1            5

(2) INFORMATION FOR SEQ ID NO:129:

(i) SEQUENCE CHARACTERISTICS:
    (A) LENGTH: 7 amino acids
    (B) TYPE: amino acid
    (C) STRANDEDNESS: single
    (D) TOPOLOGY: linear

```
    (ii) MOLECULE TYPE: peptide (ix) FEATURE:
         (A) NAME/KEY: Modified-site
         (D) OTHER INFORMATION: /note= "The Xaa at position 1 is N-
             methyl Leu."

(xi) SEQUENCE DESCRIPTION: SEQ ID NO:129:

Leu Arg Xaa Lys Tyr Pro Lys
    1               5

(2) INFORMATION FOR SEQ ID NO:130:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (D) OTHER INFORMATION: /note= "The Xaa at position 3 is N-
             methyl Leu, and that at position 5 is the D-amino acid of
             Tyr."

(xi) SEQUENCE DESCRIPTION: SEQ ID NO:130:

Leu Arg Xaa Lys Xaa Pro Lys
    1               5

(2) INFORMATION FOR SEQ ID NO:131:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (D) OTHER INFORMATION: /note= "The Xaa at position 3 is N-
             methyl Leu, and that at position 7 is the D-amino acid of
             Lys."

(xi) SEQUENCE DESCRIPTION: SEQ ID NO:131:

Leu Arg Xaa Lys Tyr Pro Xaa
    1               5

(2) INFORMATION FOR SEQ ID NO:132:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Modified-site
         (D) OTHER INFORMATION: /note= "The Xaa at position 3 is N-
             methyl Met, at position 5 is the D-amino acid of Tyr, and
             at position 7 is the D-amino acid of Leu."

(xi) SEQUENCE DESCRIPTION: SEQ ID NO:132:

Leu Arg Xaa Lys Xaa Pro Xaa
    1               5

(2) INFORMATION FOR SEQ ID NO:133:
```

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 7 is the D-
            amino acid of Leu."

(xi) SEQUENCE DESCRIPTION: SEQ ID NO:133:

Leu Arg Leu Lys Tyr Pro Xaa
        1               5

(2) INFORMATION FOR SEQ ID NO:134:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 5 is the D-
            amino acid of Tyr."

(xi) SEQUENCE DESCRIPTION: SEQ ID NO:134:

Leu Arg Leu Lys Xaa Pro Lys
        1               5

(2) INFORMATION FOR SEQ ID NO:135:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:135:

Leu Arg Leu Lys Trp Pro Lys
        1               5

(2) INFORMATION FOR SEQ ID NO:136:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 3 is Orn,
            while the Xaa at position 5 is HArg"

(xi) SEQUENCE DESCRIPTION: SEQ ID NO:136:

Leu Arg Xaa Lys Xaa Pro Lys
        1               5

(2) INFORMATION FOR SEQ ID NO:137:

```
    (i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 5 is HArg."

(xi) SEQUENCE DESCRIPTION: SEQ ID NO:137:

Leu Arg Leu Lys Xaa Pro Lys
        1               5

(2) INFORMATION FOR SEQ ID NO:138:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 2 is L-
            Cit."

(xi) SEQUENCE DESCRIPTION: SEQ ID NO:138:

Leu Xaa Met Lys Asn Pro Lys
        1               5

(2) INFORMATION FOR SEQ ID NO:139:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 2 is L-
            Cit."

(xi) SEQUENCE DESCRIPTION: SEQ ID NO:139:

Leu Xaa Asn Lys Leu Pro Lys
        1               5

(2) INFORMATION FOR SEQ ID NO:140:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:140:

Ala Arg Asn Lys Leu Pro Lys
        1               5

(2) INFORMATION FOR SEQ ID NO:141:

(i) SEQUENCE CHARACTERISTICS:
        (A) LENGTH: 7 amino acids
```

(B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:141:

Ala Arg Met Lys Asn Pro Lys
        1               5

(2) INFORMATION FOR SEQ ID NO:142:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:142:

Ala Arg Asn Lys Asn Pro Lys
        1               5

(2) INFORMATION FOR SEQ ID NO:143:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:143:

Ala Arg Asn Lys Asn Pro Phe
        1               5

(2) INFORMATION FOR SEQ ID NO:144:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:144:

Leu Arg Asn Lys Asn Pro Phe
        1               5

(2) INFORMATION FOR SEQ ID NO:145:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:145:

Leu Arg Asn Lys Asn Pro Lys
        1               5

(2) INFORMATION FOR SEQ ID NO:146:

(i) SEQUENCE CHARACTERISTICS:
            (A) LENGTH: 7 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:146:

Leu Arg Met Lys Asn Pro Phe
    1               5

(2) INFORMATION FOR SEQ ID NO:147:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 2 is L-
            Cit."

(xi) SEQUENCE DESCRIPTION: SEQ ID NO:147:

Ala Xaa Asn Lys Asn Pro Lys
    1               5

(2) INFORMATION FOR SEQ ID NO:148:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 2 is HArg."

(xi) SEQUENCE DESCRIPTION: SEQ ID NO:148:

Leu Xaa Met Lys Tyr Pro Lys
    1               5

(2) INFORMATION FOR SEQ ID NO:149:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 2 is HArg."

(xi) SEQUENCE DESCRIPTION: SEQ ID NO:149:

Leu Xaa Leu Lys Tyr Pro Lys
    1               5

(2) INFORMATION FOR SEQ ID NO:150:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:150:

Leu Lys Met Lys Tyr Pro Lys
            1               5

(2) INFORMATION FOR SEQ ID NO:151:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (D) OTHER INFORMATION: /note= "The Xaa at position 3 is HArg."

(xi) SEQUENCE DESCRIPTION: SEQ ID NO:151:

Leu Lys Xaa Lys Tyr Pro Lys
            1               5

(2) INFORMATION FOR SEQ ID NO:152:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (D) OTHER INFORMATION: /note= "The Xaa at position 7 is Cit."

(xi) SEQUENCE DESCRIPTION: SEQ ID NO:152:

Leu Arg Met Lys Tyr Pro Xaa
            1               5

(2) INFORMATION FOR SEQ ID NO:153:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (D) OTHER INFORMATION: /note= "The Xaa at position 3 is HArg."

(xi) SEQUENCE DESCRIPTION: SEQ ID NO:153:

Leu Arg Xaa Met Tyr Pro Lys
            1               5

(2) INFORMATION FOR SEQ ID NO:154:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:

(A) NAME/KEY: Modified-site
            (D) OTHER INFORMATION: /note= "The Xaa at position 3 is HArg,
                and at position 7 is Cit."

(xi) SEQUENCE DESCRIPTION: SEQ ID NO:154:

Leu Arg Xaa Lys Tyr Pro Xaa
        1               5

(2) INFORMATION FOR SEQ ID NO:155:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (D) OTHER INFORMATION: /note= "The Xaa at position 7 is Cit."

(xi) SEQUENCE DESCRIPTION: SEQ ID NO:155:

Leu Arg Met Met Tyr Pro Xaa
        1               5

(2) INFORMATION FOR SEQ ID NO:156:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:156:

Leu Arg Leu Lys Tyr Pro Asn
        1               5

(2) INFORMATION FOR SEQ ID NO:157:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:157:

Leu Arg Met Lys Tyr Pro Asn
        1               5

(2) INFORMATION FOR SEQ ID NO:158:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (D) OTHER INFORMATION: /note= "The Xaa at position 3 is HArg."

(xi) SEQUENCE DESCRIPTION: SEQ ID NO:158:

Phe Lys Xaa Met Tyr Pro Asn
        1               5

(2) INFORMATION FOR SEQ ID NO:159:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (D) OTHER INFORMATION: /note= "The Xaa at position 5 can be
            any of the following: p-chloro-Phe; p-flouro-Phe;
            p-nitro-Phe; alpha-amino-4-phenylbutyrate; beta-
            thienylanlanine (Thi); di-bromo-tyrosine; di-iodo-
            tyrosine; beta-1-napthyl-alanine; beta-2-napthyl-alanine;
            1,2,3,4-tetrahydroisoquinoline-3-carboxylic acid (Tic);
            1,2,3,4-tetrahydroisoquinoline-7-hydroxy-3-carboxylic
            acid ."

(xi) SEQUENCE DESCRIPTION: SEQ ID NO:159:

Leu Arg Met Lys Xaa Pro Lys
      1            5

(2) INFORMATION FOR SEQ ID NO:160:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:160:

Leu Arg Met Lys Leu Pro Lys Pro Pro
      1            5

(2) INFORMATION FOR SEQ ID NO:161:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:161:

Leu Arg Met Lys Leu Pro Lys Pro Pro Lys Pro Val
      1            5                10

(2) INFORMATION FOR SEQ ID NO:162:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:162:

Met Lys Leu Pro Lys Pro Pro Lys Pro Val
      1            5              10

(2) INFORMATION FOR SEQ ID NO:163:

(i) SEQUENCE CHARACTERISTICS:

```
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:163:

Leu Pro Lys Ser Ala Lys Pro Val
      1               5

(2) INFORMATION FOR SEQ ID NO:164:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:164:

Pro Lys Tyr Val Lys Gln Asn Thr Leu Lys Leu Ala Thr
      1               5                   10

(2) INFORMATION FOR SEQ ID NO:165:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:165:

Gly Pro Leu Lys Ala Glu Ile Ala Gln Arg Leu Glu
      1               5                   10
```

We claim:

1. A method for enhancing presentation of an MHC class II restricted antigenic peptide to a T cell, comprising contacting the following components under physiological conditions:

a) an MHC class II expressing antigen presenting cell;

b) mammalian invariant chain peptide consists of 4–16 contiguous amino acids of SEQ ID NO 1 and modifications thereof that retain antigen presentation enchancing activity, the peptides YRMKLPKPPKPVSKMR (SEQ ID NO: 2) and YRMKLPKSAKPVSQMR (SEQ ID NO: 3) being specifically excluded;

c) the MHC class II restricted antigenic peptide which, when added to the incubation mixture, is not in association with an antigen presenting cell; and d) a T cell which is responsive to the MHC class II restricted antigenic peptide of part c).

2. The method of claim 1 wherein the modifications thereof of step b) are selected from the group consisting of:

a) deletion of amino acids from the N-terminus;

b) deletion of amino acids from the C-terminus;

c) protection of the C-terminus;

d) protection of the N-terminus;

e) N-terminal extensions;

f) substitutions; and g) cyclized derivatives.

3. A mammalian invariant chain peptide of claim 1 wherein one or more of the amino acids is substituted with a peptidomimetic structure.

4. The method of claim 2 wherein the substitutions exclude the substitution of amino acid residues aspartate or glutamate for an amino acid found in a wild-type mammalian Ii sequence.

5. The method of claim 2 wherein the substituting amino acid is a D-isomer amino acid.

6. The method of claim 2 wherein the substituting amino acid is an N-methyl amino acid.

7. The method of claim 2 wherein the substitutions include any L-isomer amino acid or modified L-isomer amino acids.

8. The method of claim 7 wherein the modified L-amino acids are selected from the group consisting of: N-methyl leucine; L-citrulline; L-homoarginine; L-ornithine; L-hydroxyproline; p-chloro-phenylalanine; p-fluoro-phenylalanine; p-nitro-phenylalanine; α-amino-4-phenylbutyrate; β-thienylalanine; di-bromo-tyrosine; di-iodo-tyrosine; β-1-napthyl-alanine; β-2-napthyl-alanine; 1,2,3,4-tetrahydroisoquinoline-3-carboxylic acid; and 1,2,3,4-tetrahydroisoquinoline-7-hydroxy-3-carboxylic acid.

* * * * *